United States Patent [19]
Murray et al.

[11] Patent Number: 5,474,982
[45] Date of Patent: Dec. 12, 1995

[54] PDGF ANALOGS AND METHODS OF USE

[75] Inventors: Mark J. Murray; James D. Kelly, both of Seattle, Wash.

[73] Assignee: ZymoGenetics, Inc., Seattle, Wash.

[21] Appl. No.: 273,779

[22] Filed: Jul. 12, 1994

Related U.S. Application Data

[60] Continuation of Ser. No. 906,544, Jun. 30, 1992, abandoned, which is a division of Ser. No. 230,190, Aug. 8, 1988, Pat. No. 5,128,321, which is a continuation-in-part of Ser. No. 896,485, Aug. 13, 1986, Pat. No. 4,766,073, and a continuation-in-part of Ser. No. 941,970, Dec. 15, 1986, Pat. No. 4,849,407.

[51] Int. Cl.$^6$ .................................................. A61K 37/00
[52] U.S. Cl. ........................... 514/12; 530/324; 530/399; 530/300; 530/350; 514/970
[58] Field of Search .............................. 514/12; 530/300, 530/324, 350, 399

[56] References Cited

U.S. PATENT DOCUMENTS

| | | | |
|---|---|---|---|
| 4,766,073 | 8/1988 | Murray et al. | 435/172.3 |
| 4,849,407 | 7/1989 | Murray et al. | 514/12 |
| 4,861,757 | 8/1989 | Antoniades et al. | 514/21 |
| 4,874,746 | 10/1989 | Antoniades et al. | 514/21 |
| 5,128,321 | 7/1992 | Murray | 514/12 |

FOREIGN PATENT DOCUMENTS

| | | | |
|---|---|---|---|
| 171142 | 2/1986 | European Pat. Off. | C12N 15/00 |
| 177957 | 4/1986 | European Pat. Off. | C12N 15/00 |
| 243179 | 10/1987 | European Pat. Off. | A61K 37/36 |
| 282317 | 9/1988 | European Pat. Off. | C07K 13/00 |
| WO87/01728 | 3/1987 | WIPO | C12P 21/00 |
| WO88/03409 | 5/1988 | WIPO | A61K 37/26 |

OTHER PUBLICATIONS

Grotendorst et al., "Stimulation of Granulation Tissue Formation by Platelet–Derived Growth Factor in Normal and Diabetic Rats", *J. Clin. Invest.* 76:2323–2329, 1985.
Sprugel et al., "Effects of Growth Factors in Vivo", *Am. J. Pathol.* 129:601–613, 1987.
Grotendorst, "Can Collagen Metabolism Be Controll?", *J. Trauma* 24:S49–S52, 1984.
Leitzel et al., "Growth Factors and Wound Healing in the Hamster", *Dermatol. Surg. Oncol.* 11:617–622, 1985.
Rizzino et al., "Induction and Modulation of Anchorage–Independent Growth by Platelet–Derived Growth Factor, Fibroblast Growth Factor, and Transforming Growth Factor–βHd 1", *Cancer Res.* 46:2816–2820, 1986.
Lynch et al., "Role of Platelet–Derived Growth Factor in Wound Healing: Synergistic Effects with Other Growth Factors", *Proc. Natl. Acad. Sci. USA* 84:7696–7700, 1987.
Peirce et al., "In Vivo Incisional Wound Healing Augmented by Platelet–Derived Growth Factor and Recombinant c–sis Gene Homodimeric Proteins", *J. Exp. Med.* 167:974–987, 1988.
Waterfield et al, "Platelet–Derived Growth Factor is Structurally Related to Putative Transforming Protein p28 $^{sis}$ of Simian Sarcoma Virus", *Nature* 304:36–39, 1983.

Antoniades et al., "Human Platelet–Derived Growth Factor (PDGF): Amino–Terminal Amino Acid Sequence", *Science* 220:963–965, 1983.
Lawrence et al., "Reversal of an Adriamycin–Induced Healing Impairment with Growth Factors", *Surg. Forum* 36:575–577, 1985.
Graves et al., "Detection of c–sis Transcripts and Synthesis of PDGF–Like Proteins by Human Osteosarcoma Cells", *Science* 226:972–974, 1984.
Nister et al., "A Glioma–Derived Analog to Platelet–Derived Growth Factor: Demonstration of Receptor Competing Activity and Immunological Crossreactivity", *Proc. Natl. Acad. Sci. USA* 81:926–930, 1984.
Betsholtz et al., "Coexpression of a PDGF–Like Growth Factor and PDGF Receptors in a Human Osteosarcoma Cell Line: Implications for Autocrine Receptor Activation", *Cell* 39:447–457, 1984.
Tong et al., "cDNA Clones Reveal Differences Between Human Glial and Endothelial Cell Platelet–Derived Growth Factor A–Chains", *Nature* 328:619–621, 1987.
Heldine et al., "A Human Osteosarcoma Cell Line Secretes a Growth Factor Structurally Related to a Homodimer of PDGF A–Chains", *Nature* 319:511–514, 1986.
Robbins et al., "Structural and Immunological Similarities Between Simian Sarcoma Virus Gene Product(s) and Human Platelet–Derived Growth Factor", *Nature* 305:605–608, 1983.
Devare et al., "Expression of the PDGF–Related Transforming Protein of Simian Sarcoma Virus in *E. coli*", *Cell* 36:43–49, 1984.
Kurjan et al., "Structure of a Yeast Pheromone Gene (MFα): A Putative α–Factor Precursor Contains Four Tandem Copies of Mature α–Factor", *Cell* 30:933–943, 1982.
Brake et al., "α–Factor–Directed Synthesis and Secretion of Mature Foreign Proteins in *Saccharomyces cerevisiae*", *Proc. Natl. Acad. Sci. USA* 81:4642–4646, 1984.
Alber and Kawasaki, "Nucleotide Sequence of the Triose Phosphate Isomerase Gene of *Saccharomyces cerevisiae*", *Journal of Molecular and Applied Genetics* 1:419–434, 1982.
Wang et al., "A v–sis Oncogene Protein Produced in Bacteria Competes for Platelet–Derived Growth Factor Binding to Its Receptor", *J. Biological Chemistry* 259:10645–10648, 1984.

(List continued on next page.)

*Primary Examiner*—Jill Warden
*Assistant Examiner*—Benet Prickril
*Attorney, Agent, or Firm*—Seed and Berry

[57] ABSTRACT

Proteins having substantially the same biological activity as PDGF are provided. In one aspect, a protein homodimer having two polypeptide chains is disclosed, each of the chains being a mosaic of amino acid sequences substantially identical to portions of the A- and B-chains of PDGF, the protein being chemotactic or mitogenic for fibroblasts. Therapeutic compositions comprising such proteins in combination with a physiologically acceptable carrier or diluent are also provided. Such therapeutic compositions may be used within methods for enhancing the wound-healing process in warm-blooded animals.

10 Claims, 10 Drawing Sheets

OTHER PUBLICATIONS

Davis and Tai, "The Mechanism of Protein Secretion Across Membranes", *Nature* 283:433–438, 1980.

Raines et al., "Biologic Activity of Platelet–Derived Growth Factor–Related Sequences Expressed in Yeast *Saccharomyces cerevisiae*", *Biological Abstracts/RRM* No. 29014019, 1985.

Sprugel et al., "Chemotactic Activity of PDGF–Related Sequences Expressed in Yeast", *Journal of Cell Biology* 101:236A, (Abstract) 1985.

Betsholtz et al., "cDNA Sequence and Chromosomal Localization of Human Platelet–Derived Growth Factor A–Chain and Its Expression in Tumour Cell Lines", *Nature* 320:695–699, 1986.

PDGF ANALOGS AND METHODS OF USE

CROSS-REFERENCES TO RELATED APPLICATIONS

This application is a continuation of U.S. patent application Ser. No. 07/906,544, filed Jun. 30, 1992, now abandoned; which was a division of U.S. patent application Ser. No. 07/230,190, filed Aug. 8, 1988, which issued as U.S. Pat. No. 5,128,321; which was a continuation-in-part of U.S. patent application Ser. No. 06/896,485, filed Aug. 13, 1986, now U.S. Pat. No. 4,766,073 and U.S. patent application Ser. No. No. 06/941,970, filed Dec. 15, 1986, which issued as U.S. Pat. No. 4,849,407.

TECHNICAL FIELD

The present invention relates to the production of PDGF analogs, and to the use of those analogs in enhancing the wound-healing process in warmblooded animals.

BACKGROUND OF THE INVENTION

Human platelet-derived growth factor (PDGF) has been shown to be the major mitogenic protein in serum for mesenchymal-derived cells. This is well documented by numerous studies of platelet extracts or purified PDGF induction of either cell multiplication or DNA synthesis (a prerequisite for cell division) in cultured smooth muscle cells, fibroblasts and glial cells (Ross et al., *Proc. Natl. Acad. Sci U.S.A.* 71:1207, 1974; Kohler and Lipton, *Exp. Cell Res.* 87:297, 1974; Westermark and Wasteson, *Exp. Cell Res.* 98:170, 1976; Heldin et al., *J. Cell Physiol.* 105:235, 1980; Raines and Ross, *J. Biol. Chem.* 257:5154, 1982). Furthermore, PDGF is a potent chemoattractant for monocytes and for cells that are responsive to it as a mitogen (Grotendorst et al., *J. Cell Physiol.* 113:261, 1982; Seppa et al., *J. Cell Biol.* 92:584, 1982). Due to its mitogenic activity, PDGF is useful as an important component of a defined medium for the growth of mammalian cells in culture, making it a valuable research reagent with multiple applications in the study of animal cell biology.

In vivo, PDGF normally circulates stored in the alpha granules of platelets. Injury to arterial endothelial linings causes platelets to adhere to the exposed connective tissue and release their granules. The released PDGF is thought to chemotactically attract fibroblasts and smooth muscle cells to the site of injury and to induce their focal proliferation as part of the process of wound repair (Ross and Glomset, *N. Eng. J. of Med.* 295:369, 1976).

It has been postulated that as a part of this response to injury, PDGF released by platelets may play a causative role in the development of the proliferative lesions of atherosclerosis (Ross and Glomset, ibid.) which is one of the principal causes of myocardial and cerebral infarction. Strategies for the prophylaxis and treatment of atherogenesis in the past have been narrowly directed toward reducing risk factors for the disease, such as lowering blood pressure in hypertensive subjects and reducing elevated cholesterol levels in hypercholesterolemic subjects.

While natural PDGF may be isolated from human plasma or platelets as starting material, it is a complex and expensive process, in part due to the limited availability of the starting material. In addition, it is difficult to purify PDGF with high yield from other serum components due to its extremely low abundance and biochemical properties. Furthermore, the therapeutic use of products derived from human blood carries the risk of disease transmission due to contamination by, for example, hepatitis virus, cytomegalovirus, or HIV. It is therefore desirable to produce proteins having the biological activity of PDGF through the use of genetically engineered host cells.

In view of PDGF's clinical applicability in the treatment of injuries in which healing requires the proliferation of fibroblasts or smooth muscle cells and its value as an important component of a defined medium for the growth of mammalian cells in culture, the production of useful quantities of protein molecules with activities similar to those of authentic PDGF is clearly invaluable.

In addition, the ability to produce relatively large amounts of PDGF or PDGF analogs would be a useful tool for elucidating the putative role of the v-sis protein, $p28^{sis}$, in the neoplastic process.

Further, since local accumulation of smooth muscle cells in the intimal layer of an arterial wall is central to the development of atherosclerotic lesions (Ross and Glomset, ibid.), one strategy for the prophylaxis and treatment of atherosclerosis would be to suppress smooth muscle cell proliferation. The ability to produce large amounts of PDGF or PDGF analogs would be useful in developing inhibitors or designing specific therapeutic approaches which prevent or interfere with the in vivo activity of PDGF in individuals with atherosclerosis.

DISCLOSURE OF THE INVENTION

Briefly stated, the present invention discloses a variety of proteins which have substantially the same biological activity as PDGF. In one aspect of the present invention, a protein homodimer having two polypeptide chains is disclosed, each of the chains being a mosaic of amino acid sequences substantially identical to portions of the A- or B-chains of PDGF, the protein being chemotactic or mitogenic for fibroblasts. For purposes of the present invention, "substantially identical" polypeptide chains are those chains that are at least 80% homologous to one another at the amino acid level. Within the present invention, the phrase "substantially homologous" refers to those sequences that are at least 30% homologous to one another. Within certain embodiments, the protein is unglycosylated. In addition, proteins are disclosed in which the chains are substantially identical to the A-chain of PDGF, as shown in FIGS. 3A–3G.

Within another aspect of the present invention, substantially pure protein homodimers having two polypeptide chains, each of the chains being substantially identical to the A-chain of PDGF, as shown in FIGS. 3H or 3I, are disclosed.

Within yet another aspect of the present invention, therapeutic compositions are disclosed comprising the proteins briefly described above in combination with a physiologically acceptable carrier or diluent. Within a related aspect of the present invention, methods for enhancing the wound-healing process in warm-blooded animals are disclosed. The methods generally comprise administering to the animal a therapeutically effective amount of one or more of the proteins described above, and a physiologically acceptable carrier or diluent. Within one embodiment of the present invention, the proteins are administered with an effective amount of basic fibroblast growth factor.

These and other aspects of the invention will become evident upon reference to the following detailed description and attached drawings.

BRIEF DESCRIPTION OF THE DRAWINGS

FIGS. 3A–3I illustrate the amino acid sequences of representative polypeptides of the invention. Amino acids are designated by the standard one-letter codes.

BEST MODE FOR CARRYING OUT THE INVENTION

Figure 1:
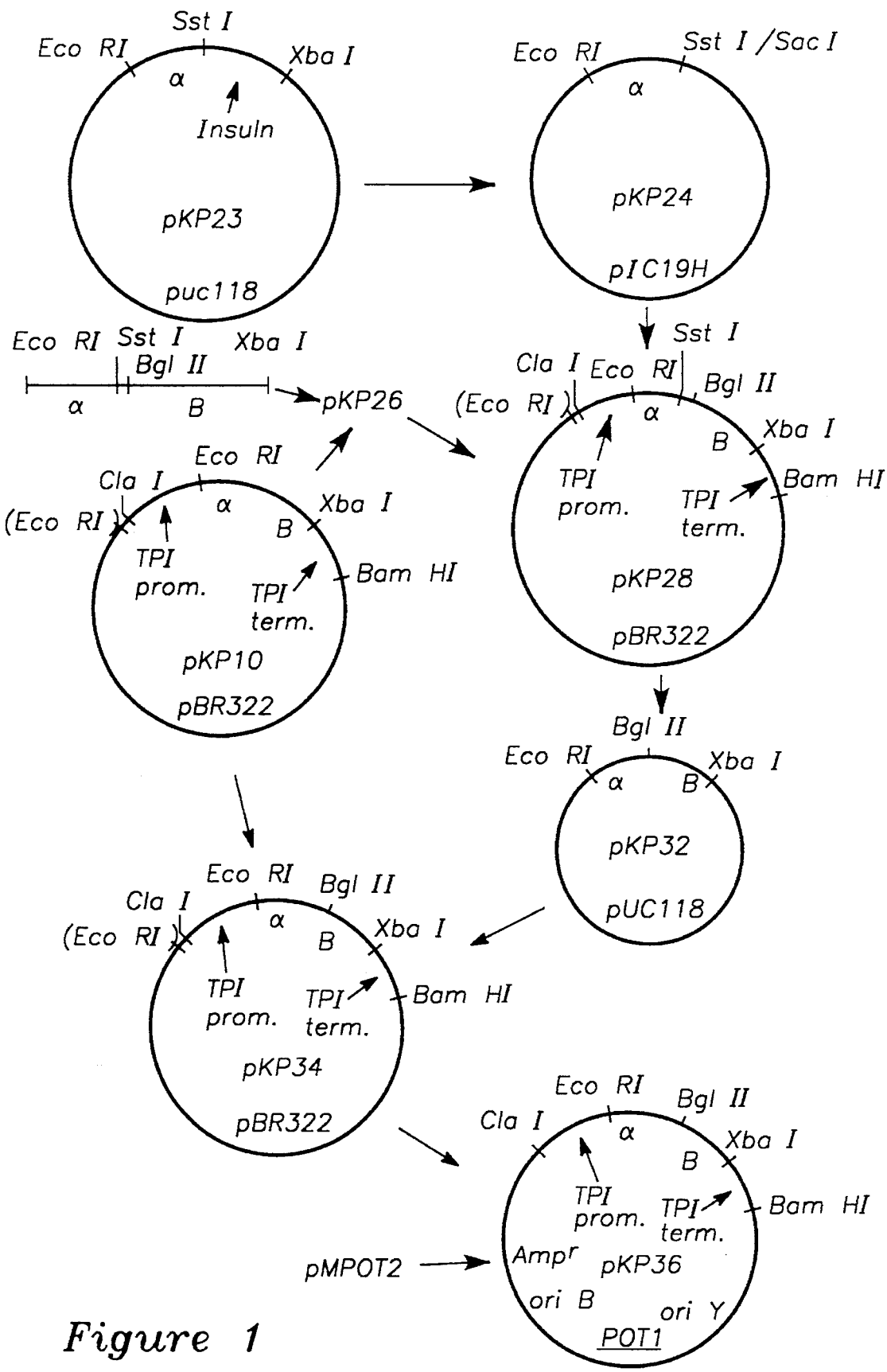
FIG. 1 illustrates the construction of the expression vector pKP36. Symbols used are α, yeast α-factor leader; B, PDGF B-chain; Amp^r, ampicillin resistance gene; ori B, bacterial origin of replication; ori Y, yeast origin of replication; POT1, *S. pombe* triose phosphate isomerase gene.

Prior to setting forth the invention, it may be helpful to an understanding thereof to set forth definitions of certain terms to be used hereinafter.

Polypeptide: A polymer of amino acids.

Reading Frame: The arrangement of nucleotide codons which encode an uninterrupted stretch of amino acids. During translation of an mRNA, the proper reading frame must be maintained. For example, the sequence GCUGG-UUGUAAG may be translated into three reading frames or phases, depending on whether one starts with G, with C, or with U, and thus may yield three different peptide products. Translation of the template begins with an AUG codon, continues with codons for specific amino acids, and terminates with one of the translation termination codons.

Coding Sequence: DNA sequences which in the appropriate reading frame directly code for the amino acids of a protein.

Complementary DNA: or cDNA. A DNA molecule or sequence which has been enzymatically synthesized from the sequences present in an mRNA template, or a clone of such a molecule.

Secretory Signal Sequence: That portion of a gene or cDNA encoding a signal peptide. A signal peptide is the amino acid sequence in a secretory protein which signals its translocation into the secretory pathway of the cell. Signal peptides generally occur at the beginning (amino terminus) of the protein and are approximately 20–40 amino acids long with a stretch of about 9–10 hydrophobic amino acids near the center. Very often the signal sequence is proteolytically cleaved from the protein during the process of secretion.

Cell Surface Receptor: A protein molecule at the surface of a cell which specifically interacts with or binds a molecule approaching the cell's surface. Once the receptor has bound the cognate molecule, it effects specific changes in the physiology of the cell.

Mitogen: A molecule which stimulates cells to undergo mitosis. Mitosis is asexual somatic cell division leading to two daughter cells, each having the same number of chromosomes as the parent cell.

Transformation: The process of stably and hereditably altering the genotype of a recipient cell or microorganism by the introduction of purified DNA. This is typically detected by a change in the phenotype of the recipient organism.

Transcription: The process of producing a mRNA template from a structural gene.

Expression: The process, starting with a structural gene or cDNA, of producing its polypeptide, being a combination of transcription and translation. An expression vector is a plasmid-derived construction designed to enable the expression of a gene or cDNA carried on the vector.

Plasmid: An extrachromosomal, double-stranded DNA sequence comprising an intact "replicon" such that the plasmid is replicated in a host cell. When the plasmid is placed within a unicellular organism, the characteristics of that organism may be changed or transformed as a result of the expression of the DNA sequences of the plasmid. For example, a plasmid carrying the gene for tetracycline resistance (tet^R) transforms a cell previously sensitive to tetracycline into one which is resistant to it.

Yeast Promoter: DNA sequences upstream from a yeast gene which promote its transcription.

Biological Activity: Some function or set of activities performed by a molecule in a biological context (i.e., in an organism or an in vitro facsimile). In the case of PDGF, these biological activities include the induction of chemotaxis and/or mitogenesis of responsive cell types, following the binding of PDGF to specific cell surface receptors. Other biological effects of human platelet PDGF may include: phospholipase activation; increased phosphatidylinositol turnover and prostaglandin metabolism; stimulation of both collagen and collagenase synthesis by responsive cells; an indirect proliferative response of cells lacking PDGF receptors; and potent vasoconstrictor activity.

PDGF Analog: A polypeptide which is substantially homologous to at least a portion of the A-chain or the B-chain of PDGF, or both, wherein the polypeptide exhibits the biological activity of PDGF as defined herein.

The novel proteins of the present invention can be distinguished from PDGF isolated from platelets. Platelet PDGF is known to be composed of two polypeptide chains, an A-chain and a B-chain, which are held together by disulfide bonds to form the biologically active dimer molecule(s).

The present invention provides for the production of PDGF analogs of known composition and activity in genetically engineered eucaryotic cells. Suitable host cells include yeast cells, especially *Saccharomyces cerevisiae*, other fungal cells (e.g., Aspergillus) and cultured cells from multicellular organisms, such as mammals, insects, fish, birds, etc. Production of PDGF analogs in eucaryotic cells is generally disclosed by Murray et al. (U.S. patent application Ser. Nos. 660,496; 705,175; 896,485; 941,970; 942,161; and 942,484 which are incorporated herein by reference).

The present invention provides for the production of a variety of PDGF analogs, including homodimers and heterodimers of A-chain and B-chain, as well as homodimers of A-chain and B-chain variants. These analogs include homodimers of 125-amino acid and 110-amino acid A-chain polypeptides. In another embodiment, dimers of polypeptides which are mosaics of A- and B-chain sequences are produced. The term "mosaic," as used within the present invention, denotes a polypeptide which includes contiguous portions of the A-chain and B-chain sufficient to encode a molecule having biological activity as defined herein. The constituent portions of the mosaic can be chosen from wild-type A-chain and B-chain, as well as variants or derivatives of the A-chain or B-chain. The portions of the mosaic may range from 1 to approximately 75 amino acids or more in length, provided that the overall primary structural features of the A-chain and B-chain are maintained. The common structural features of the A-chain and B-chain are the relative positions of (a) the cysteine residues; (b) the regions of amino acid charge; and (c) regions of hydrophobic and hydrophilic character. In addition, it may be useful to maintain the blocks of sequence identity between the A- and B-chains. In one embodiment these hybrid polypeptides were designed to alter the binding specificity of the A- and B-chains. Data indicate that sequences between B-chain amino acids 25 to 34 are important for B-chain-specific binding. Hybrids of particular interest include those which substitute amino acids in this region of B-chain for the corresponding amino acids of A-chain.

DNA sequences encoding the PDGF analogs of the present invention may be obtained from the v-sis gene or from cDNAs encoding the native A-chain or B-chain of PDGF, or suitable sequences may be synthesized according to standard procedures (Murray et al., ibid.). Amino acid substitutions may be produced by in vitro site-specific mutagenesis according to standard procedures, or may be produced through enzymatic cleavage and ligation of suitable DNA fragments.

For example, a human A-chain cDNA may be isolated from a human cDNA library made from an appropriate source of messenger RNA by using the v-sis gene or a fragment thereof as a hybridization probe, or through use of oligonucleotide probes designed from the A-chain DNA or amino acid sequence (see, for example, Betsholtz et al., *Nature* 320:695–699, 1986, and Tong et al., *Nature* 328:619–621, 1987). Preferred sources of mRNA include human transformed cell lines, e.g., U2–OS and T-24. These cells can be cultured in vitro and are known to secrete a protein having PDGF-like activity (Heldin et al., *Nature* 319:511–514, 1986). The identity of this cDNA as that encoding A-chain may be verified by DNA sequencing.

A human B-chain cDNA may be isolated from a cDNA library made from an appropriate source of mRNA using the v-sis gene or a fragment thereof as a hybridization probe, or through the use of oligonucleotide probes designed from the B-chain sequence. A preferred source of mRNA in this regard is human umbilical vein endothelial cells. These cells can be cultured in vitro for short periods of time and are known to secrete PDGF (Di Corletto and Bowen-Pope, *Proc. Natl. Acad. Sci. U.S.A.* 80:1919, 1983) and contain high levels of B-chain mRNA. A human c-sis cDNA clone is disclosd by Clarke et al. (*Nature* 308:464–467, 1984). Proteins produced according to the present invention may be glycosylated or unglycosylated. Although the native human A-chain is glycosylated, the coding sequence may be modified to remove the carbohydrate attachment site. The concensus glycosylation sequence Asn-X-Ser/Thr is perferably altered to Gln-X-Ser/Thr, although as will be apparent to those skilled in the art, other amino acid substitutions may be made.

Once an appropriate DNA sequence encoding a protein exhibiting PDGF-like biological activity is obtained, the sequence is ligated to an appropriate secretory signal sequence, promoter and terminator. The resulting expression unit is then inserted into a vector which is used to transfect or transform the selected host cells. Selection of promoters, terminators, secretion signals and vector sequences appropriate to a specific host is within the level of ordinary skill in the art.

Yeast cells are a particularly preferred host. Promoters which may be utilized in yeast include the yeast alpha-factor (MFα1) promoter and the yeast triose phosphate isomerase (TPI1) promoter (Kawasaki, U.S. Pat. No. 4,599,311). Promoters may also be obtained from other yeast genes, e.g., alcohol dehydrogenase 1 (ADH1) and alcohol dehydrogenase 2 (ADH2). In yeast, secretion of the PDGF analogs is accomplished through use of a secretory signal sequence such as the pre-pro sequence of the yeast mating pheromone alpha-factor (Kurjan and Herskowitz, *Cell* 30:933, 1982; Julius et al., *Cell* 36:309, 1984; and Brake et al., *PNAS* 81:4642, 1984). Other secretion signals may also be used, including the a-factor (Brake, EP 123,289), PHO5 (Le Montt et al., WO 86/00638) and SUC2 (Carlson and Botstein, *Cell* 28:145–154, 1982) secretory signal sequences. To ensure the efficient transcription termination and polyadenylation of mRNA, a yeast terminator sequence, such as the TPI1 terminator (Alber and Kawasaki, *J. Molec. Genet. Appl.* 1: 419, 1982), is added. The expression unit constructions are then inserted into an appropriate expression vector. Expression vectors will generally include an origin of replication and a selectable marker, although integration of the exogenous expression unit into the host genome is within the scope of the present invention. It is preferable to use an expression vector which is stably maintained at a high copy number within the host cell in order to produce more biological activity per unit of culture. Suitable yeast expression vectors in this regard include the plasmids pCPOT, pMPOT2 (Murray et al., ibid.) and PRPOT, which include the *Schizosaccharomyces pombe* gene encoding the glycolytic enzyme triose phosphate isomerase (POT1 gene). Inclusion of the POT1 gene ensures the stable maintenance of the plasmid in an appropriate host cell having a deletion in the triose phosphate isomerase gene due to its ability to complement the host cell gene deletion. Other selection systems may also be used, such as the leu2 selection system described by Beggs (*Nature* 275:104–109, 1978).

Expression vectors prepared as described above are then transformed into a yeast host having a genetic defect which can be complemented by the selectable marker. Yeast strains having such defects are widely available, such as from American Type Culture Collection, Rockville, Md., or the Yeast Genetic Stock Center, Berkeley, Calif., or may be prepared using standard techniques of mutation and selection. Procedures for transforming yeast are well known in the literature (see, for example, Beggs, ibid. and Hinnen et al., *Proc. Natl. Acad. Sci. U.S.A.* 75:1929–1933, 1978).

The transformed yeast cells may be selected by growth on conventional complex medium containing glucose when a POT1-based vector is utilized. A conventional medium, such as YEPD (20 grams glucose, 20 grams Bactopeptone, 10 grams yeast extract per liter), may be used. Once selected, transformants containing the appropriate expression constructions are grown to stationary phase on conventional complex media, the cells removed by centrifugation or filtration, and the medium concentrated. PDGF analogs are purified by immunoaffinity using monoclonal antibodies or by other conventional techniques including precipitation and fractionation by a variety of chromatographic methods.

Using a variety of assays, it can be demonstrated that spent media from yeast cultures expressing the PDGF analogs possess biological activities substantially identical to authentic human PDGF.

Expression of biologically active PDGF analogs in eucaryotic cells other than yeast cells can be achieved by a person skilled in the art through use of appropriate expression/regulatory signals. Transcriptional promoters capable of directing the expression of these sequences are chosen for their ability to give efficient and/or regulated expression in the particular eucaryotic cell type. A variety of promoters are available, including viral (e.g., SV40 and adenovirus) and cellular (e.g., metallothionein gene; U.S. Pat. Nos. 4,601,978 and 4,579,821) promoters. Signal sequences capable of directing the gene product into the cell's secretory pathway are chosen for their function in the particular host cell type. Other useful regulatory signals, such as transcription termination signals, polyadenylation signals and transcriptional enhancer sequences, are also chosen for their function in the host cell, the selection of which would be apparent to an individual skilled in the art. Methods for transforming mammalian cells and expressing cloned DNA sequences therein are described by Kaufman and Sharp (*J. Mol. Biol.* 159:601–621, 1982), Southern and Berg (*J. Mol. Appl. Genet.* 1:327–341, 1982), and Neumann et al. (*EMBO J.* 1:841–845, 1982). Methods for expression of cloned genes in cells derived from other higher eucaryotes are disclosed by, for example, Miyajima et al. (*Gene* 58:273–282, 1987), Isa and Shima (*J. Cell Sci.* 88:219–224, 1987) and Kretsovali et al. (*Gene* 58:167–176, 1987).

According to the present invention, it is possible to produce recombinant PDGF-like molecules which are homodimers or heterodimers. To produce heterodimers, two different expression units are introduced into the same cell and heterodimers are isolated from the biologically active products by immobilized metal affinity chromatography (Sulkowski, in *Protein Purification: Micro to Macro*, 149–162, Alan R. Liss, Inc., 1987; Porath et al., *Nature* 258:598, 1975) or immunoaffinity chromatography using isotype-specific monoclonal antibodies as disclosed in U.S. patent application No. 139,960. The expression units may be on different expression vectors with different selectable markers or, preferably, on a single expression vector. The second strategy offers the advantage of providing equal copy numbers of the two expression units.

The techniques of cell culture have advanced considerably in the last several years as have the number and varieties of mammalian cells which will grow in culture. Central to these advances is a better understanding of the nutritional requirements (i.e., hormones and growth factors) of cultured cells (Barnes and Sato, *Cell* 22:649, 1980). This understanding permits the formulation of defined, serum-free culture media. The PDGF analogs of the present invention are useful as components of these defined media.

The proteins described herein are also suitable for use within therapeutic compositions for enhancing the wound-healing process in warm-blooded animals. The normal wound-healing process in warm-blooded animals proceeds by an orderly series of events involving the interaction of chemoattractants, growth factors, and a variety of specialized cell types. This process includes an ordered migration and, in some cases, the subsequent proliferation of a number of these specialized cell types into the wound space, and involves the complex interaction of a variety of biologically active factors. This process is discussed in detail in Hunt et al., eds., *Soft and Hard Tissue Repair; Biological and Clinical Aspects*, Praeger Publishers, New York, 1984, which is incorporated herein by reference. Briefly, tissue injury results in the release of chemotactic factors which attract particular cell types, which then release additional and/or other chemoattractant or mitogenic factors. These factors, in turn, affect additional specialized cells, ultimately restoring the injured tissue. Further, there is evidence that the rate at which this process normally proceeds is limited by the levels of chemoattractants and growth factors at the wound site, and may be enhanced by the addition of these agents (Grotendorst et al., *J. Clin. Invest.* 76:2323–2329, 1985, herein incorporated by reference).

The wound-healing process in the dermis begins with the formation of a clot from the blood which flows into the wound. This results in a cross-linked network of fibrin molecules binding the wound together. During this process, platelets adhere to the injured tissue, becoming activated, and release the contents of their alpha granules. The disruption of the dermal tissue, the blood coagulation reactions, and platelet activation all generate molecules which cause the migration of a series of new cells into the wound, thereby initiating the repair process.

Among the contents of the alpha granules released by the platelets is PDGF. In addition, other contents of the alpha granules and by-products of the coagulation reactions induce the appearance of macrophages. Macrophages are a second important source of PDGF in the wound. The deposition of PDGF at the site of an injury provides a chemotactic stimulus for fibroblasts to enter the wound space and a mitogenic stimulus for the fibroblasts to subsequently proliferate therein, thereby participating in the process of repair. An important role of the fibroblast is the regeneration of connective tissue at the wound site. The fibroblasts proliferate in the wound and deposit collagen types I and II and other extracellular proteins to the connective tissue matrix. The presence of new fibroblasts and their protein products reconstitutes the dermal architecture such that it can be re-epithelialized and the wound thereby healed.

Similarly, the wound-healing process in relation to the repair of connective tissue also requires fibroblast infiltration and proliferation, leading to subsequent collagen deposition.

The proteins of the present invention have been shown to possess substantially the same biological activity as authentic PDGF. The basic biological activity of PDGF, particularly the induction of chemotaxis and mitogenesis in responsive cell types (including fibroblasts and smooth muscle cells), underlies many of the physiological roles of this protein, including its role in tissue repair.

Because the chemotactic and mitogenic properties of PDGF are central to its role in the wound-healing process, the biologically active proteins of the present invention have similar therapeutic utility. These biologically active proteins are therefore expected to have clinical applicability in the treatment of wounds in which healing requires the migration and/or proliferation of fibroblasts. In addition, PDGF acts as a chemotactic and mitogenic agent for smooth muscle cells, the proliferation of which may contribute to the healing of certain wounds. Smooth muscle cells will be affected by PDGF in a manner similar to that described above for fibroblasts, thereby contributing to the healing process.

The proteins of the present invention are expected to accelerate the healing process in a broad spectrum of wound conditions. For purposes of the present invention, the terms "wound" or "wound condition" include any disruption of the dermal layer of the skin. Examples of disruptions to the dermal layer include chronic non-healing dermal ulcers (which can have a variety of causes), superficial wounds and lacerations, abrasions, surgical wounds, and some burns. In addition, wounds may also result in damage to connective tissue, the repair of which involves fibroblast proliferation and collagen deposition. The proteins of the present invention are of general utility in enhancing the wound-healing process, and are particularly useful in conditions in which the normal wound-healing process is suppressed or inhibited. For example, normal wound-healing may be retarded by a number of factors, including advanced age, diabetes, cancer, and treatment with anti-inflammatory drugs, steroids or anticoagulants, and the proteins described herein may be used to offset the delayed wound-healing effects of such treatments. These PDGF analogs are particularly useful in promoting wound healing in diabetic animals.

For therapeutic use in the applications described herein, the proteins of the present invention are preferably administered topically in combination with a physiologically acceptable carrier or diluent. Further, it is preferable to use a substantially pure preparation of the protein, that is, one which is generally free of impurities or contaminants which would interfere with its therapeutic use. Particularly preferred are those preparations which are free of toxic, antigenic, inflammatory or other deleterious substances, and are greater than 80% pure. The proteins will be delivered in a volume sufficient to cover the wound. A therapeutically effective amount sufficient to accelerate the rate of appearance and increase the number of new fibroblasts in the wound space and to stimulate DNA synthesis in and collagen deposition by those fibroblasts, will typically be in the range of about 0.5–10.0 µg per cm$^2$ of wound area, depending upon the characteristics of the wound. The therapeutic compositions according to the present invention may be reapplied at one- to several-day intervals until healing is complete. Treatment will generally include administration of the above-described doses on a daily basis for between 5 and 30 days, although the particular treatment regimen will be determined by the nature of the wound.

Therapeutic compositions according to the present invention comprise the proteins described herein in combination with suitable carriers, as well as adjuvants, diluents, or stabilizers. Typically, the proteins described herein will be used in a concentration of about 10 to 100 µg/ml of total volume, although it will be apparent that concentrations in the range of 1 µg/ml to 1000 µg/ml may be used. Suitable adjuvants include collagen or hyaluronic acid preparations, fibronectin, factor XIII, polyethylene glycol, or other proteins or substances designed to stabilize or otherwise enhance the active therapeutic ingredient(s). Diluents include albumins, saline, sterile water, mannitol, etc. Other stabilizers, antioxidants, or protease inhibitors may also be added. Alternatively, the proteins may be applied to wounds or wound dressings as aqueous solutions.

The therapeutic compositions of the present invention may also contain other pharmaceutically active ingredients, for example, heparin, which has been shown to accelerate the healing of thermal burns. Other growth factors, such as TGF-γ, TGF-β, EGF, basic FGF, platelet factor 4, insulin or somatomedins (see Grotendorst et al., 1985) and angiogenesis factor, may also work synergistically with the PDGF analogs described herein. In a preferred embodiment, PDGF analogs are combined with basic fibroblast growth factor (basic FGF). Antibiotics may also be included to keep the wound free of infection.

The following examples are offered by way of illustration, and not by way of limitation.

EXAMPLES

Restriction endonucleases and other DNA modifying enzymes were obtained from Bethesda Research Laboratories, New England Biolabs or Boehringer Mannheim Biochemicals and generally used according to the supplier's instructions.

Oligonucleotides were synthesized on an Applied Biosystems model 380A DNA synthesizer and purified by polyacrylamide gel electrophoresis. Oligonucleotides were labeled with gamma-$^{32}$P-ATP using protein kinase.

In vitro site-specific mutagenesis was performed by the two primer method essentially as described by Zoller and Smith (*DNA* 3:479–488, 1984) using the universal second primer ZC87 (Table 2) or by the one primer method (Zoller and Smith, *Nuc. Acids Res.* 10:6487–6500, 1982; Zoller and Smith, *Meth. Enzymology* 100:468–500, 1983).

General cloning procedures and methods for transforming *E. coli* are described by Maniatis et al. (*Molecular Cloning: A Laboratory Manual*, Cold Spring Harbor Laboratory, Cold Spring Harbor, N.Y., 1982). Yeast cells were transformed essentially as described by Beggs (*Nature* 275:104–108, 1978) and Hinnen et al. (*Proc. Natl. Acad. Sci. U.S.A.* 75:1929–1933, 1978).

PDGF activity assays were performed according to published procedures. The radioreceptor assay for PDGF was performed essentially as described by Bowen-Pope and Ross (*J. Biol. Chem.* 257:5161, 1982) using subconfluent monolayers of human diploid fibroblasts. Mitogenic activity was assayed by measurement of $^3$H-thymidine incorporation as described by Raines and Ross (*Meth. Enzymology* 909:749–773, 1985). The down regulation assay for measurement of receptor binding was performed as described by Hart et al. (*Science* 240:1529–1531, 1988). Briefly, human dermal fibroblasts grown in 24-well culture dishes (3×10$^4$ cells per well) were incubated for two hours at 37° C. with increasing concentrations of PDGF isoforms. The cells were then washed to remove unbound ligand and incubated for two hours at 4° C. with labeled PDGF isoforms. Cells were washed, harvested and lysed, and cell-associated label was determined.

Receptor binding was also measured by binding competition assays. B-chain specific binding was assayed by incubating multiple dilutions of, conditioned yeast media with SK5 fibroblasts in 24-well trays for two hours in the presence of 1 ng/ml $^{125}$I-BB. A mutant BB containing a phenylalanine to tyrosine substitution at amino acid 23 was used for iodination. A standard curve was generated with purified BB and the ability of the test sample to compete with the labeled ligand was compared to the standard curve. For A/B receptor binding, the assay used D1 Swiss 3T3 cells and a standard curve generated with $^{125}$I-AA.

Platelet PDGF (AB isoform) was isolated as disclosed by Hart (U.S. patent application Ser. No. 139,960) using monoclonal antibodies 120.1.2.1.2 (produced from a hybridoma deposited with American Type Culture Collection under accession number HB 9610) and 121.6.1.1.1 (produced from hybridoma ATCC HB 9613) coupled to CNBr-activated Sepharose (Pharmacia, Piscataway, N.J.). A platelet lysate sample was frozen and thawed and any precipitate was removed by centrifugation at 35,000×g for 60 minutes at 4° C. The sample was then loaded onto the antibody 120.1.2.1.2-Sepharose column. This antibody column binds only the BB isoform of PDGF. The sample was cycled over the column for three hours at 4° C. The antibody 121.6.1.1.1-Sepharose column was then added in series with the first column (120.1.2.1.2-Sepharose) and the sample cycled for 12 hours at 4° C. This column binds the AB and BB isoforms of PDGF, but the removal of the BB isoform by the first column (120.1.2.1.2-Sepharose) resulted in the binding of only AB-dimer material on the second column. The columns were washed in series with 200 ml of PBS (pH 7.2), 0.5M Nacl. The 121.6.1.1.1 column was then eluted with 0.1M glycine, pH 2.5. The peak fractions for PDGF activity, determined by radioreceptor assay (as described above), were pooled and chromatographed by HPLC on a Micro Pak SP C18 column (Varian, Palo Alto, Calif.) using a 0–100% acetylnitrile gradient containing 0.1% trifluoracetic acid. The peak fractions containing PDGF activity, as determined by radioreceptor assay, were pooled and lyophilized.

EXAMPLE 1

Optimization of Protein Expression

A. Optimized B-Chain Expression Construction

The DNA sequences encoding the alpha-factor leader and PDGF B-chain were modified to contain yeast-optimal codons and to encode wild-type alpha-factor as well as authentic human B-chain. This allowed the optimization of B-chain expression levels. Construction of the optimized expression unit is illustrated in FIG. 1.

The codon-optimized alpha-factor leader sequence was obtained from an expression vector containing the gene for the insulin analog B(129)-Ala-Ala-Lys-A( 1–21) (Markussen et al., EP 163,529). An Eco RI-Xba I fragment comprising the alpha-factor pre-pro and insulin sequences was cloned into Eco RI, Xba I digested pUC118 (obtained from J. Vieira and J. Messing, Waksman Institute of Microbiology, Rutgers, Piscataway, N.J.; described by Vieira and Messing, *Meth. Enzymology* 153, 1987 [in press]) and single-stranded template DNA was prepared. This template was then mutagenized according to the two-primer method (Zoller and Smith, *DNA* 3:479–488, 1984) using the mutagenic oligonucleotide ZC862 (5' CGA ATC TTT TGA GCT CAG AAA CAC C 3'). The mutagenesis resulted in the creation of an Sst I site at the 3' end of the alpha-factor leader. A correctly altered plasmid was selected and designated pKP23. The leader sequence was excised from pKP23 by digestion with Eco RI and Sst I, and the leader fragment was subcloned into Eco RI and Sac I-cut pIC19H (Marsh et al., *Gene* 32:481–486, 1984). The resultant plasmid was designated pKP24.

The human B-chain sequence was obtained from plasmid pB12. (Plasmid pB12 is disclosed by Murray et al., allowed U.S. patent application Ser. No. 896,485. Briefly, pB12 comprises a DNA sequence encoding human PDGF B-chain operatively linked to the *S. cerevisiae* TPI1 promoter, MFα1 pre-pro sequence and TPI1 terminator.) pB12 was digested with Eco RI and Xba I and the α-factor/B-chain fragment was recovered. Plasmid pKP10, comprising the TPI1 promoter—alpha-factor—VSB—TPI 1 terminator of pSB1 (Murray et al., U.S. Ser. No. 896,485) inserted into a pBR322 vector lacking an Eco RI site, was digested with Eco RI and Xba I to remove the α-factor/VSB sequence. The pB12 α-factor/B-chain sequence was then inserted into the pKP10 expression unit. The resultant plasmid was designated pKP26.

The yeast codon-optimized alpha-factor sequence was then introduced into the expression unit. Plasmid pKP26 was cut with Eco RI and Sst I to remove the α-factor sequence. The codon-optimized α-factor sequence was then removed from pKP24 as an Eco RI-Sst I fragment and joined to the linearized pKP26. The resultant vector was designated pKP28.

The Sst I site introduced into the alpha-factor leader to facilitate vector construction was then removed to restore the wild-type coding sequence. Plasmid pKP28 was digested with Eco RI and Xba I and the alpha-factor—B-chain fusion sequence was recovered. This fragment was cloned into pUC118 and single-stranded template DNA was isolated. The template was mutagenized by the two primer method using the mutagenic oligonucleotide ZC1019 (5' ACC CAA GGA TCT CTT GTC CAA AGA AAC ACC TTC TTC 3'). A correctly mutagenized plasmid was designated pKP32.

The entire expression unit was then reconstructed. Plasmid pKP32 was digested with Eco RI and Xba I and the alpha-factor-B-chain fragment was recovered. This fragment was inserted into Eco RI, Xba I cut pKP10 to construct pKP34. Plasmid pKP34 was digested with Cla I and Bam HI and the expression unit was recovered. This fragment was inserted into Cla I, Bam HI digested pMPOT2 (a yeast 2 micron-based plasmid containing yeast and bacterial replication origins, ampicillin resistance gene and POT1 selectable marker) to construct pKP36.

The B-chain sequence was then codon optimized. An internal Bgl II—Sph I fragment of the B-chain sequence of pKP36 was replaced with a sequence assembled from the oligonucleotides shown in Table 1. The pMPOT2-based expression vector containing the fully optimized expression unit was designated pB170m.

TABLE 1

| | Sequence (5'→3') |
|---|---|
| ZC886 | GGCCACCATGTGTTGAAGTTCAAAGATGCTCGGGTTGTTGTAACAACAGAA ACGTTCAATG |
| ZC887 | TCGACATTGAACGTTTCTGTTGTTACAACAACCCGAGCATCTTTGAACTTC AACACATG |
| ZC888 | GATCTCTAGAAGATTGATCGACAGAACCAACGCCAACTTCTTGGTTT |
| ZC889 | GTGGCCAAACCAAGAAGTTGGCGTTGGTTCTGTCGATCAATCTTCTAGA |
| ZC907 | CGTTAGAAAGAAGCCAATCTTCAAGAAGGCTACCGTTACCCTCGAGGACCA CTTGGCATG |
| ZC908 | TCGACCAACCCAAGTTCAATTGCGGCCGGTTCAAGTGCGCAAGATCGAAA T |
| ZC909 | CTAACGATTTCGATCTTGCGCACTTGAACCGGCCGCAATTGAACTTGGGTT GG |

| TABLE 1-continued | |
| --- | --- |
| | Sequence (5'→3') |
| ZC910 | CCAAGT GGT CCT CGA GGGT AAC GGT AGC CTT CTT GAA GAT T GGC TT CTTT |

B. Optimized A-Chain Expression Construction

Figure 2:
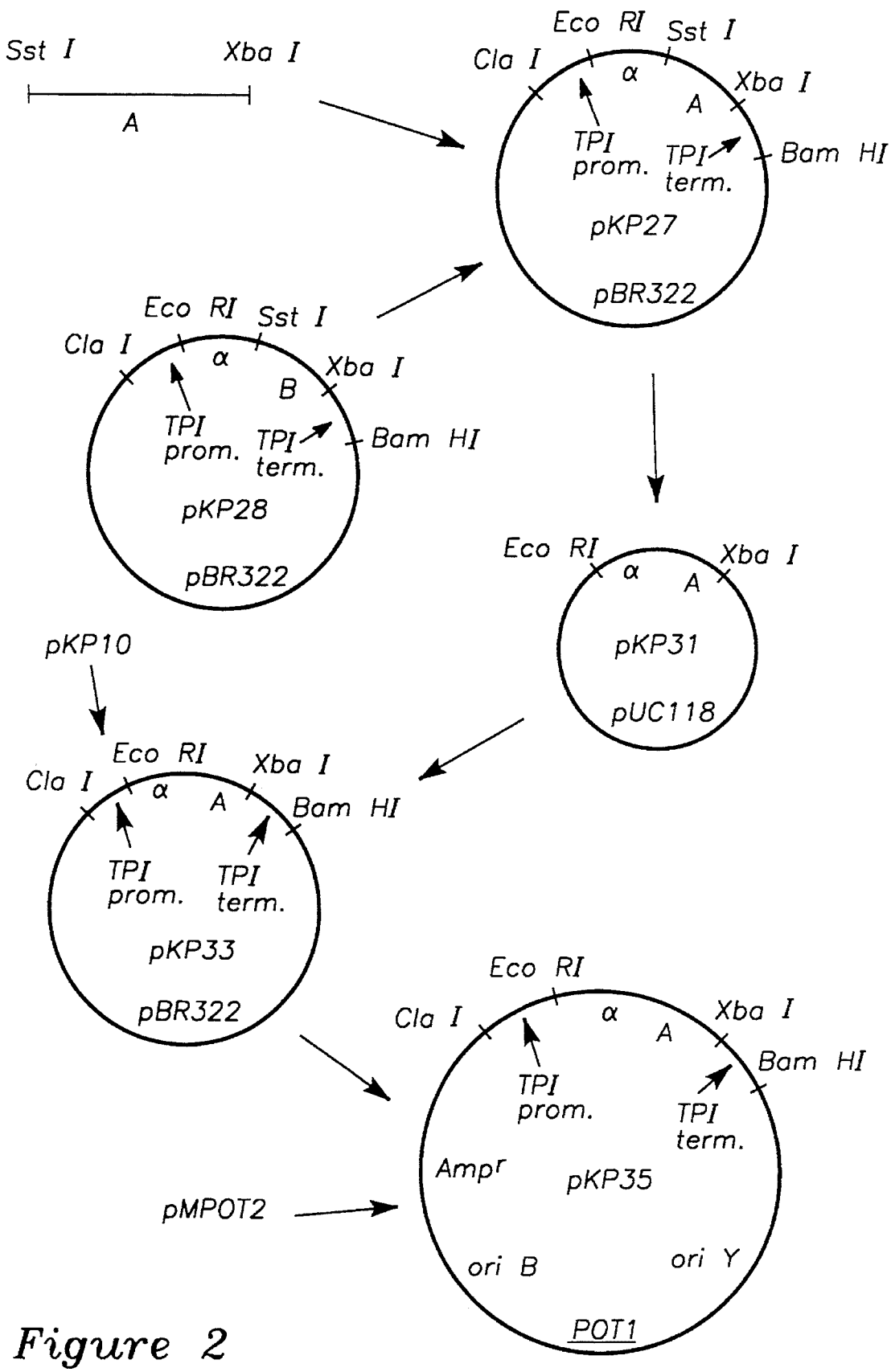
FIG. 2 illustrates the construction of the expression vector pKP35. A indicates the PDGF A-chain sequence. Other symbols are used as in FIG. 1.

The codon-optimized A-chain sequence from plasmid pA7 (Murray et al., allowed U.S. patent application No. 896,485 and Example 2, below) was combined with the codon-optimized alpha-factor leader sequence in a series of construction steps parallel to those described above for B-chain (FIG. 2). The pA7 A-chain sequence was isolated as a Sst I-Xba I fragment and inserted into Sst I, Xba I-cut pKP28 to construct pKP27. Plasmid pKP27 was digested with Eco RI and Xba I and the alpha-factor—A-chain fragment was cloned into pUC118.

Mutagenesis, using the oligonucleotide ZC1018 (5' TTC GAT AGA TCT CTT GTC CAA AGA AAC ACC TCC TTC 3'), was carried out as described above to remove the Sst I site and restore the wild-type alpha-factor sequence. The corrected plasmid was designated pKP31.

A codon-optimized expression vector was then constructed. Plasmid pKP31 was digested with Eco RI and Xba I and the alpha-factor—A-chain fragment was joined to Eco RI, Xba I cut pKP10. The resultant vector, designated pKP33, contained the entire expression unit. Plasmid pKP33 was digested with Cla I and Bam HI and the expression unit fragment was recovered. This fragment was inserted into Cla I, Bam HI cut pMPOT2 to construct the expression vector pKP35.

C. Expression of A-Chain and B-Chain

S. cerevisiae strain XB13–5B (MATα leu2,3–112 ura3 bar1 gal2 tpi1::LEU2) was separately transformed with plasmids pB170m and pKP35 according to standard procedures. Transformants were cultured in glucose media at 30° C. with agitation. Cultures were harvested, cells were removed by centrifugation, and protein was purified from the supernatants.

S. cerevisiae strain XB13–5B transformants containing plasmids pB170m and pKP35 have been deposited with American Type Culture Collection, Rockville, Md. 20852, U.S.A under accession numbers 20863 and 20862, respectively.

D. Protein Purification

Yeast culture supernatants, prepared as described above, are concentrated using Millipore Pellicon Cassettes (Millipore, Bedford, Mass.).

The concentrates are pelleted by centrifugation in a Beckman J-6B centrifuge (Beckman Instruments, Inc., Brea, Calif.) at 4200 rpm for 30 minutes to remove the turbidity. EDTA is added to a final concentration of 10 mM and the pH of the mixtures is adjusted to pH 5.5 with 5M NaOH. The concentrates are then diluted with water to a conductivity of about 10 millimhos.

The resultant concentrates are chromatographed on an S-Sepharose Fast Flow (Pharmacia, Piscataway, N.J.) column. The column is washed with 20 mM sodium phosphate, 0.1M sodium chloride, pH 7.3. The column is then eluted with 20 mM sodium phosphate, 1M sodium chloride, pH 7.3. The absorbance at 280 nm of the eluate is followed and the peak fractions are collected and pooled.

The eluates are frozen at −20° C. and then thawed. The particulate material is removed from the eluates by centrifugation. The supernatants are harvested and the pH adjusted to 3.0 with 0.87M acetic acid. The eluates are then concentrated using an Amicon YM10 filter (Amicon, Danvers, Mass.). The concentrated eluates are diluted with five volumes of 1M acetic acid to lower the sodium chloride concentration to about 0.2M.

The eluates are then chromatographed on a second S-Sepharose column. The column is washed with 1M acetic acid and the absorbance at 280 nm of the eluates is followed until it returns to baseline. The column is eluted with 1M acetic acid, 1.5M ammonium chloride, pH 4.8–5.0. The $A_{280}$ of the eluates is followed and the PDGF isoforms are harvested as the last $A_{280}$ peak. The peak fractions are pooled and concentrated using an Amicon YM10 filter.

The concentrated eluates are then applied to a Sephadex G-50 Superfine (Pharmacia, Piscataway, N.J.) column using a sample volume of about 1% of the column volume. The column is run at a flow rate of 5 cm/hr in 1M ammonium acetate pH 9.0. The purest fractions, as determined by SDS-gel electrophoresis, are pooled and the pH adjusted to 4.0 with acetic acid.

EXAMPLE 2

A/B Mosaic Polypeptides

A. Construction of pA3

The A-chain coding sequences were inserted into the pSB1 vector as short synthetic oligonucleotide duplexes designed to encode known A-chain amino acid sequence (Johnson et al., EMBO J. 3:921–928, 1984). ZC545 and ZC546 (Table 2) were annealed, creating a short duplex DNA fragment with a 5' Sst I cohesive end, a unique Mlu restriction site, and a 3' Bgl II cohesive end. This duplex was cloned into Sst I and Bgl II-digested pSB1. One µl of pSB1 vector (0.15 pmole) was combined with 1 µl of ZC546 (≈1.6 pmole) and 0.6 µl of ZC545 (≈1.5 pmole), plus 0.25 µl of 0.3M NaCl (final NaCl concentration in the annealing reaction is 30 mM) and the mixture was heated to 60° C. for five minutes. After heating, the mixture was brought to room temperature and then placed on ice. Then 0.5 µl of 10X ligase buffer (0.5M Tris-HCl, 0.1M $MgCl_2$, 2M DTT, 0.01 M ATP, pH 7.8), 0.1 µl of $T_4$ DNA ligase (New England Biolabs) and 2.5 µl of water were added and this ligation mixture was diluted and used to transform E. coli HB1010 cells. Ampicillin-resistant, plasmid-bearing colonies were picked, grown up and plasmid DNA isolated by the "miniprep" method of Ish-Horowicz and Burke (Nuc. Acid Res. 9:2989–2998, 1981). The plasmids were analyzed for the presence of an Sst I-Bgl II insert and a new Mlu I restricion site and confirmed by DNA sequence analysis. The ZC545–546 duplex encoded A-chain amino acids alanine 8 through tryosine 17 and the resulting plasmid was termed pA1.

ZC547 and ZC548 (Table 2) were annealed to create a second short Sst I—Bgl II fragment encoding A-chain amino acids serine 1 through arginine 13 and also containing an Mlu I restriction site. The ZC547–548 duplex was separately cloned into Sst I and Bgl II digested pSB1. One μl of pSB1 (1.5 pmole) digested with Sst I and Bgl II was combined with 2 μl of ZC547 (1 pmole) and 2 μl of ZC548 (1 pmole) plus 0.25 μl of 0.3 M NaCl and the mixture was heated to 50° C. for five minutes. After heating, this annealing mixture was brought to room temperature and then placed on ice. Then 0.6 μl of 10X ligase buffer and 0.1 μl of T$_4$ DNA ligase (New England Biolabs) were added and the reaction was incubated overnight at 12° C. An aliquot of this ligation reaction was diluted and used to transform E. coli HB101 cells and the resulting plasmids were screened and analyzed as described above for pA1. The resulting plasmid was termed pA2.

The overlapping pA1 and pA2 A-chain coding regions were joined at the unique Mlu I restriction site using conventional techniques. Plasmid pA2 was digested with Mlu I and Bam HI and the ≈1.4 kb vector (pUC containing) fragment was isolated by agarose gel electrophoresis and extracted from the agarose with CTAB (Langridge et al., Anal. Biochem. 103:264–271, 1980). Plasmid pA1 was also digested with Mlu I and Bam HI and the ≈800 base pair fragment, encoding A-chain amino acids 13 through 17 fused to B-chain amino acids 24 through 109 followed by the TPI terminator, was isolated and extracted as above. Equimolar amounts of these two fragments were ligated under standard conditions and an aliquot used to transform E. coli HB101 cells. Plasmids obtained from ampicillin-resistant colonies were analyzed by restriction enzyme digestion for the correct fragments and confirmed by DNA sequencing. The resulting plasmid termed pA3 thus encoded a hybrid protein beginning with A-chain amino acids 1 through 17 followed in frame by B-chain amino acids 24 through 109. The Cla I—Bam HI fragment of pA3 containing the entire expression unit was cloned into pMPOT2 and the resulting plasmid pA3m was transformed into yeast.

S. cerevisiae strain E18 #9 was transformed with pA3m and transformants were grown in fermentation medium for two days at 30° C. Cells were removed by centrifugation and the medium was assayed for mitogenic activity. Results indicated that the medium contained approximately 175 ng/ml of PDGF activity.

B. Construction of pA6

Further addition of A-chain amino acids to the A–B hybrid was accomplished in a similiar fashion. Plasmid pA3 was digested first with Asp718, which cuts the plasmid once in the A-chain sequence at proline codon 7, and with Bam HI, and the hybrid amino acid coding fragment subcloned into pUC118. This subclone was termed pA3N and was subsequently digested with Bgl II and Bst XI. Bgl II cuts at the boundary of the A- and B-chain sequences in the hybrid and Bst XI cuts approximately 40 base pairs downstream in the B-chain. The vector fragment (pUC-containing) from this digest was isolated by agarose gel electrophoresis and extracted with CTAB. One picomole each of oligonucleotides ZC692 and ZC693 (Table 2) was annealed to form a short DNA duplex with a 5' Bgl II end and a 3' Bst XI end. This duplex encoded A-chain glutamic acid 18 through phenylanine 31 and was ligated with 0.1 picomole of Bgl II-Bst XI-digested pA3N. The ligation was performed overnight and the ligated products transformed into E. coli MV1193 cells. The resulting plasmid termed pA6N now has extended the A-chain amino acid sequence to the Bst XI site at amino acid A31 followed by B-chain amino acids B38 through B109.

Plasmid pA6N was then digested with Asp718 and Bam HI and the A-B hybrid fragment cloned back into Asp718-Bam HI digested pA3m. This new A-B hybrid plasmid is termed pA6m and encodes A-chain amino acid sequence up to amino acid 40 because the Bst XI site lies at the start of a region of high homology between A- and B-chains.

S. cerevisiae strain E18 #9 was transformed with pA6m and transformants were grown in fermentation medium for two days at 30° C. Cells were removed by centrifugation and the medium was assayed for mitogenic activity. Results indicated that the medium contained between approximately one and three ug of PDGF activity per ml.

C. Construction of pA7

The remainder of the A-chain sequence was constructed from oligonucleotides in a similar manner, incorporating unique restriction sites introduced in order to facilitate subcloning and sequencing the synthetic oligonucleotide sequences. All the oligonucleotides were synthesized on an Applied Biosystems 380-A DNA synthesizer. Oligonucleotides ZC752 and ZC753 (Table 2), each 87mers, were annealed and subcloned as a Hind III—Xba I fragment encoding A-chain amino acids 77–104. ZC752 and ZC753 (1.25 picomole each) were annealed in 5 μl of 40 mM NaCl by heating to 65° C. for 15 minutes and then allowing the mixture to come to room temperature and putting on ice. One-tenth of this annealed duplex (0.0125 picomole) was ligated into both pUC118 (0.07 pmole) and M13mp18 (0.02 picomole) which were previously digested with Hind III and Xba I. The ligated mixtures were used to transform the appropriate E. coli host strain JM107 in the case of M13mp18 and MV1193 in the case of pUC118) and the resulting plasmid or RF DNAs were analyzed by restriction endonuclease digestion and DNA sequencing.

The oligonucleotides ZC746+747, 748+ 749, and 750+ 751 (Table 2) were designed to form short duplexes with cohesive ends which when joined would constitute the sequence between the Bst XI site at A-chain codon 31 and the Hind III site at A-chain codon 77. The ZC748/749 duplex encodes a glutamine at A-chain residue 48 instead of the asparagine which is present in the native polypeptide. This change destroys the N-linked gylcosylation site at this position. The oligocleotides were phosphorylated with $^{32}$p and T$_4$ polynucleotide kinase under standard conditions. The pairs ZC746+ZC747, ZC748+ZC749, and ZC750+ZC751 were each annealed by combining 2.5 pmole of each oligonucleotide in 5 μl of 40 mM NaCl, heating to 65° C. for 15 minutes, allowing to come to room temperature, and putting on ice. The three annealing mixtures were combined (now 15 μl) and ligated in final volume of 20 μl. The ligated products were electrophoresed in a 4% NuSieve agarose gel (FMC Corporation) in TBE buffer (90 mM Tris, 90 mM boric acid, 2 mM disodium EDTA) followed by autoradiography. The ≈140 base pair fragment corresponding to the three correctly ligated duplexes was cut out of the the gel and extracted with CTAB. This fragment, together with the previously cloned Hind III-Xba I fragment, was ligated into the Bst XI-Xba I digested pA6N vector. The resulting plasmid was termed pA6N+. Plasmid pA6N+ was then digested with Asp718 and Xba I and the A-chain coding fragment was cloned back into pA3. This plasmid, designated pA7, encodes the entire mature A-chain with the Asn to Gln substitution.

D. Construction of pA12

Figure 3A:
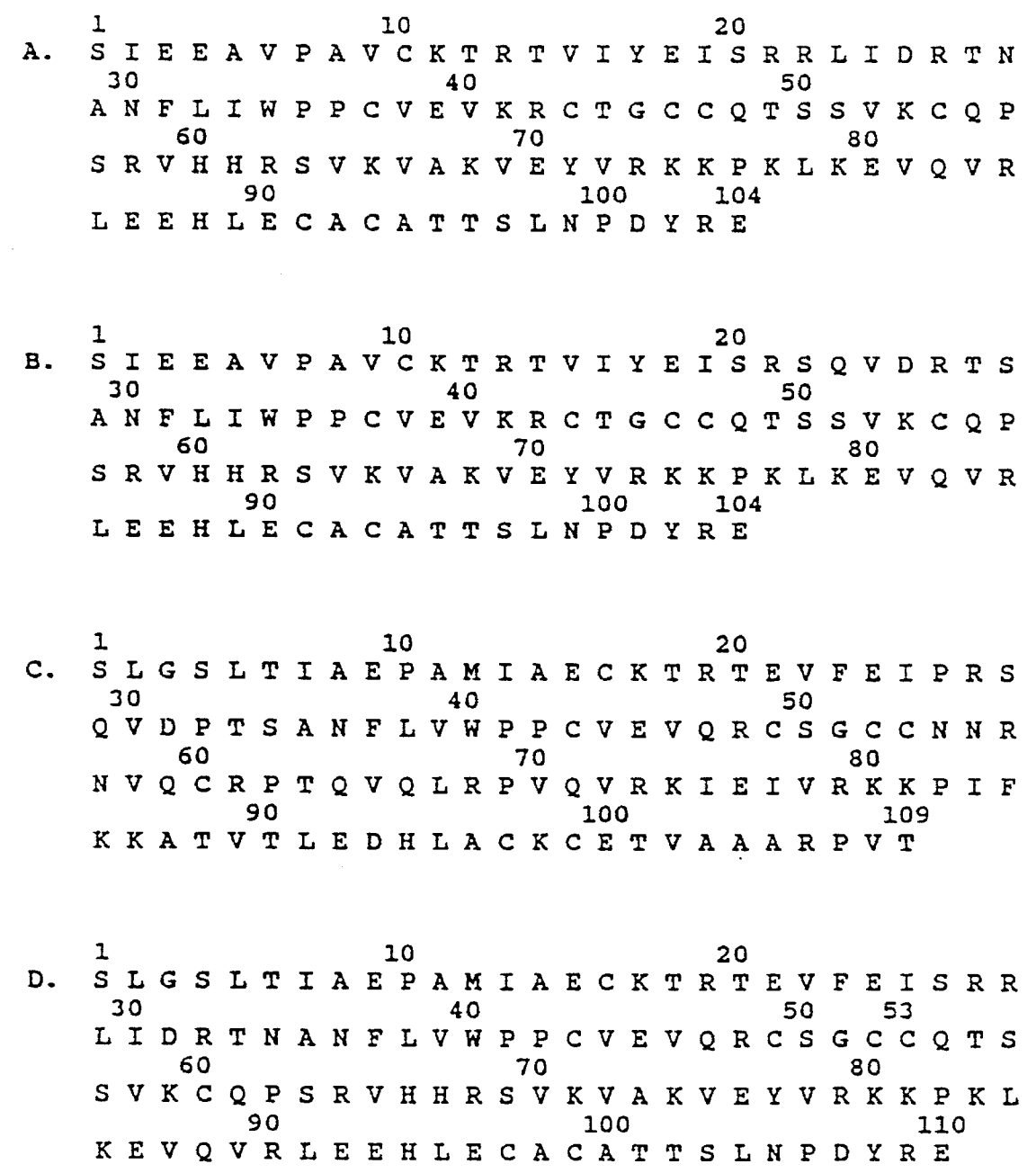

The A-chain coding sequence was altered by replacing A-chain amino acids 20–28 with the corresponding B-chain sequence. The sequence of the encoded polypeptide is shown in FIG. 3A. The ca. bp Asp 718-Xba I pA7 fragment was cloned into Asp 718, Xba I-cut M13mp18 and single-stranded template DNA was prepared. The codon substitutions were made by site-specific mutagenesis using the mutagenic oligonucleotide ZC1830 (Table 2). Plaques were screened using $^{32}$p-labeled ZC1830 and positives were confirmed by sequence analysis. A positive clone was selected, digested with Asp 718 and Sty I and the 181 bp A–B hybrid fragment was isolated. This fragment was inserted into the A7 expression unit in A7CB/19R (comprising the codon-optimized A-chain expression unit as a Cla I-Bam HI insert in pIC19R) which had been cut with Asp 718 and Sty I. Clones were screened for the appearance of Bgl II and Bsm I sites. A positive clone was selected and digested with Cla I and Bam HI. The 2.2 kb expression unit fragment was isolated and cloned into Cla I, Bam HI-cut pMPOT2. The resultant expression vector was designated pA12m.

TABLE 2

| Oligonucleotide | Sequence (5'→3') |
| --- | --- |
| ZC87 | TCC CAG TCA CGA CGT |
| ZC545 | GAT CTC GTA GAT AAC GGT ACG CGT CTT ACA AAC AGC TCT CTT GAG CT |
| ZC546 | C AAG AGA GCT GTT TGT AAG ACG CGT ACC GTT ATC TAC GA TGT TTA TCC AAA CTA CTA TTG CC GCC ATT TTC CCA ATC CAC CAA T |
| ZC547 | TGT TTA TCC AAA CTA CTA TTG CC |
| ZC548 | GCC ATT TTC CCA ATC CAC CAA T |
| ZC692 | GAT CCC AAG ATC CCA AGT TGA CCC AAC CTC TGC CAA CTT C |
| ZC693 | TTG GCA GAG GTT GGG TCA ACT TGG GAT CTT GG |
| ZC746 | TT GAT TT GGC CAC CAT GT GTT GAA GTT AAG AGA T GT ACT GGG T GT |
| ZC747 | CAGT ACA TCT CTT AAC TT CAA CAC AT GGT GGC CAA AT CAA GA AG |
| ZC748 | T GT CAA ACC T CGA GT GTT AAG T GT CAA CCA T CC AGA GT |
| ZC749 | GAT GGT T GA CAC TT AAC ACT CGA GGT TTT GAC AAC ACC |
| ZC750 | T C ACC ACA GAT CCG TT AAG GTT GCC AAG GTT GAA T ACG TT AG AAA GAA GCC AA |
| ZC751 | AGC TTT GGC TTC TTT CT AAC GT ATT CAA CCT TGG CAA CCT T A ACG GAT CT GT GGT GAA CTC T G |
| ZC752 | AGC TT AAG GAA GTT CAA GTT AGA TT GGA AGA ACA CTT GGA AT GT GCA T GCG CT ACC ACC T CTT T GAA CCC AGA CT ACA GAG AAT AAT |
| ZC753 | CT AGA TT ATT CT CT GT AGT CT GGG TT CAA AGA GGT GGT AGC G CAT GCA CAT T CC AAG T GTT CTT CCA AT CT AAC TT GAA CTT CC TTA |
| ZC1016 | AAT TTA TCG ATA AGC TTG ACT CGA GAG TCG ACT CTA GAG GAT CCG |
| ZC1017 | AGC TCG GAT CCT CTA GAG TCG ACT CTC GAG TCA AGC TTA TCG ATA |
| ZC1370 | GGA TCC TCT AGA TTA TCT AAC GTC GGT GTC TTC TTC TCT GTA GTC TG |
| ZC1462 | GGA TCC TCT AGA TTA AGT TGG CTT GAA TCT CTT TCT CTT TCT CTT CTT ACC AGA TTC TCT TGG TCT ACC GGT GTC TTC TTC TC |
| ZC1600 | TCG GGT TGT TGT AAC ACC |
| ZC1601 | TCG AGG TGT TAC AAC AAC |
| ZC1602 | TCG AGG TTT GAC AAC AAC |
| ZC1603 | TCG GGT TGT TGT CAA ACC |
| ZC1604 | TCG AGA GCT CAA TG |
| ZC1605 | TCG ACA TTG AGC TC |
| ZC1606 | TCG AGG GTA ACG GTA GCC TTC TTG AAG ATT GGC TTC TTT CTT ACG TAT TCA AC |

TABLE 2-continued

| Oligonucleotide | Sequence (5'→3') |
| --- | --- |
| ZC1607 | CAA GGT TGA ATA CGT AAG AAA GAA GCC AAT CTT CAA GAA GGC TAC CGT TAC CC |
| ZC1830 | CA AAT CAA GAA GTT GGC ATT CGT TCT GTC GAC CAA TCT TCT AGA GAT CTC GTA GAT AAC G |
| ZC1831 | GAA GTT GGC AGA GGT TCT GTC GAC TTG GGA TCT AGA GAT CTC GTA GAT AAC G |

E. Construction of pa13

Figure 3B:
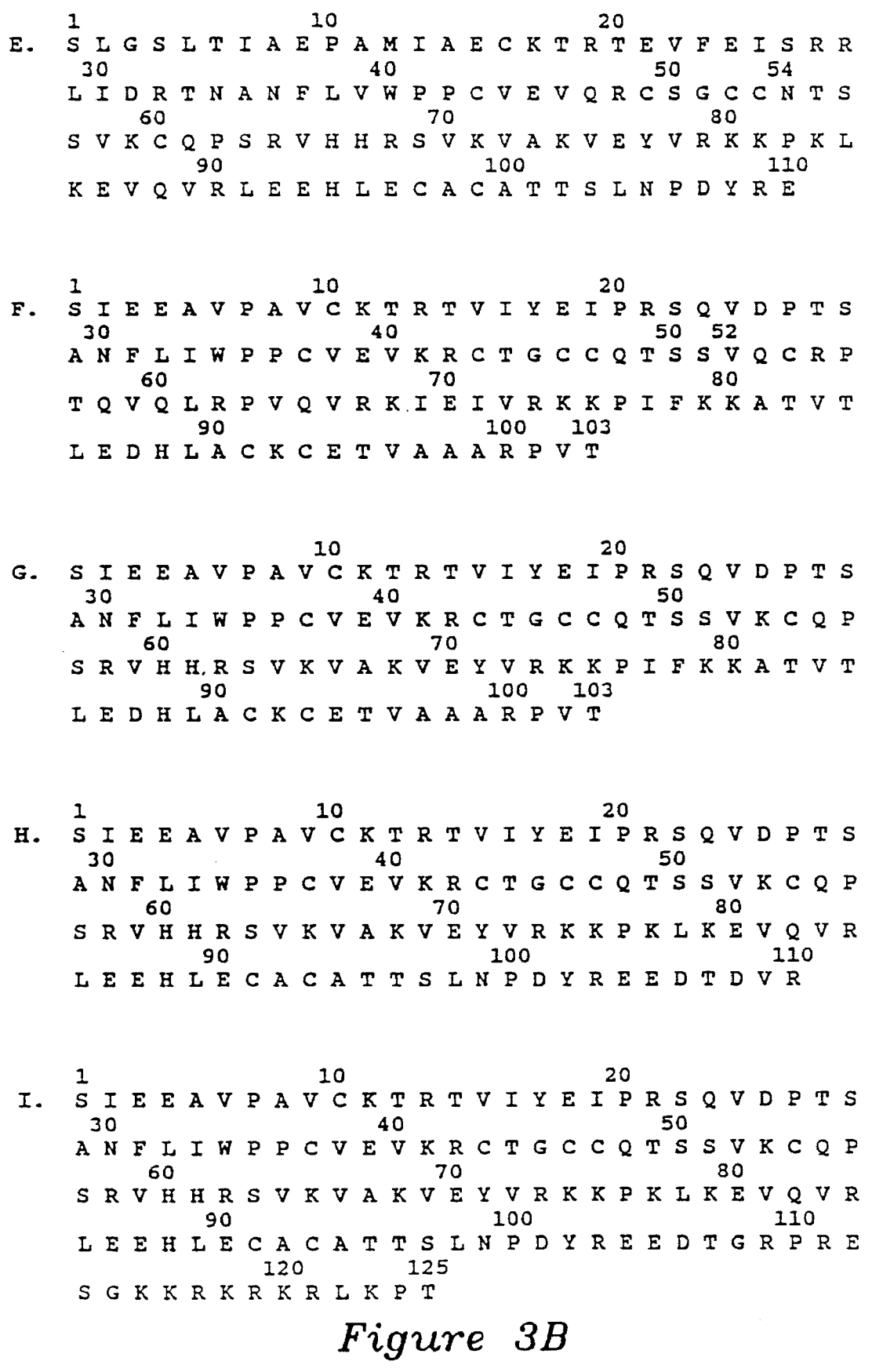

The A-chain coding sequence was altered by replacing proline residues at positions 20 and 26 with the equivalent B-chain amino acids serine and arginine, respectively (FIG. 3B). To prepare a template for mutagenesis, the ca. 300 bp Asp 718-Xba I A7 fragment was isolated and cloned into M13mp18 which had been cut with the same enzymes. Single-stranded template was prepared and mutagenized using the mutagenic primer ZC1831 (Table 2). Plaques were screened by hybridization to $^{32}$P-labeled ZC1831 and positive clones were confirmed by sequence analysis. A sequence confirmed positive clone was digested with Asp 718 and Sty I and the 181 bp fragment was isolated. This fragment was inserted into the A7 expression unit in A7CB/19R which had been cut with Asp 718 and Sty I. Clones were screened for the appearance of Bgl II and Sal I sites. A positive clone was selected and digested with Cla I and Bam HI. For expression vector construction the 2.2 kb expression unit fragment is isolated and cloned into Cla I, Bam HI-cut pMPOT2 to construct vector pA13m.

F. Construction of B26

B-chain amino acids 26–34 were replaced with the corresponding A chain sequence. The sequence of this hybrid polypeptide is shown in FIG. 3C. An Eco RI-Xba I subclone of the codon-optimized B-chain sequence (Example 1) in pUC118 was digested with Bgl II and Bst XI and the 7.9 kb fragment containing vector and B-chain sequences was isolated. Oligonucleotides ZC692 and ZC693 (Table 2) were annealed and the resulting double-stranded fragment was ligated to the 7.9 kb fragment. Plasmid clones were screened for the loss of Bgl II and Xba I sites. The A–B hybrid sequence was isolated from a positive clone by digestion with Eco RI and Xba I, and the fragment was cloned into Eco RI, Xba I cut plasmid B12CB/pBR (a plasmid identical to pKP28, see Example 1). The hybrid expression unit was then isolated as a Cla IBam HI fragment and subcloned into Cla I, Bam HI-cut pMPOT2. Clones were confirmed by sequence analysis of an Eco RI-Xba I fragment inserted into M13mp18. A confirmed positive clone was designated pB26m.

Plasmid pB26m was transformed into *S. cerevisiae* strain XB13–5B, and transformants were grown for two days at 30° C. in fermentation medium (Table 3). Cells were removed by centrifugation, and the medium was assayed for mitogenic activity and found to be positive.

TABLE 3

| Fermentation Medium |
| --- |
| 20 g NZ Amine Type A |
| 7 g KH$_2$PO$_4$ |
| 6 g NH$_4$SO$_4$ |

TABLE 3-continued

| Fermentation Medium |
| --- |
| 2 g MgSO4 |

Dissolve the solids in water and bring the volume to one liter. Autoclave for 25 minutes. After autoclaving add 2 ml/l Trace Elements Solution (recipe following), 3 ml Vitamin Solution (recipe following), 2M sodium succinate, pH 5.5 to a final molarity of 0.1M and 50% glucose to a final concentration of 2%.

Trace Elements Solution 9.45 mg ZnSO$_4$ 284.8 mg Fe$_2$(SO$_4$)$_3$ 48 mg CuSO$_4$·5H$_2$O Dissolve the solids in distilled water and bring to a final volume of 100 ml. Filter sterilize.

Vitamin Solution 20 mg riboflavin 5.4 g pantothenic acid 6.1 g niacin 1.4 g pyrodoxin 60 mg biotin 40 mg folic acid 6.6 g inositol 1.3 g thiamine Dissolve in distilled water and bring to a final volume of one liter. Filter sterilize.

G. Construction of B/A53 and B/A54

Figure 4:
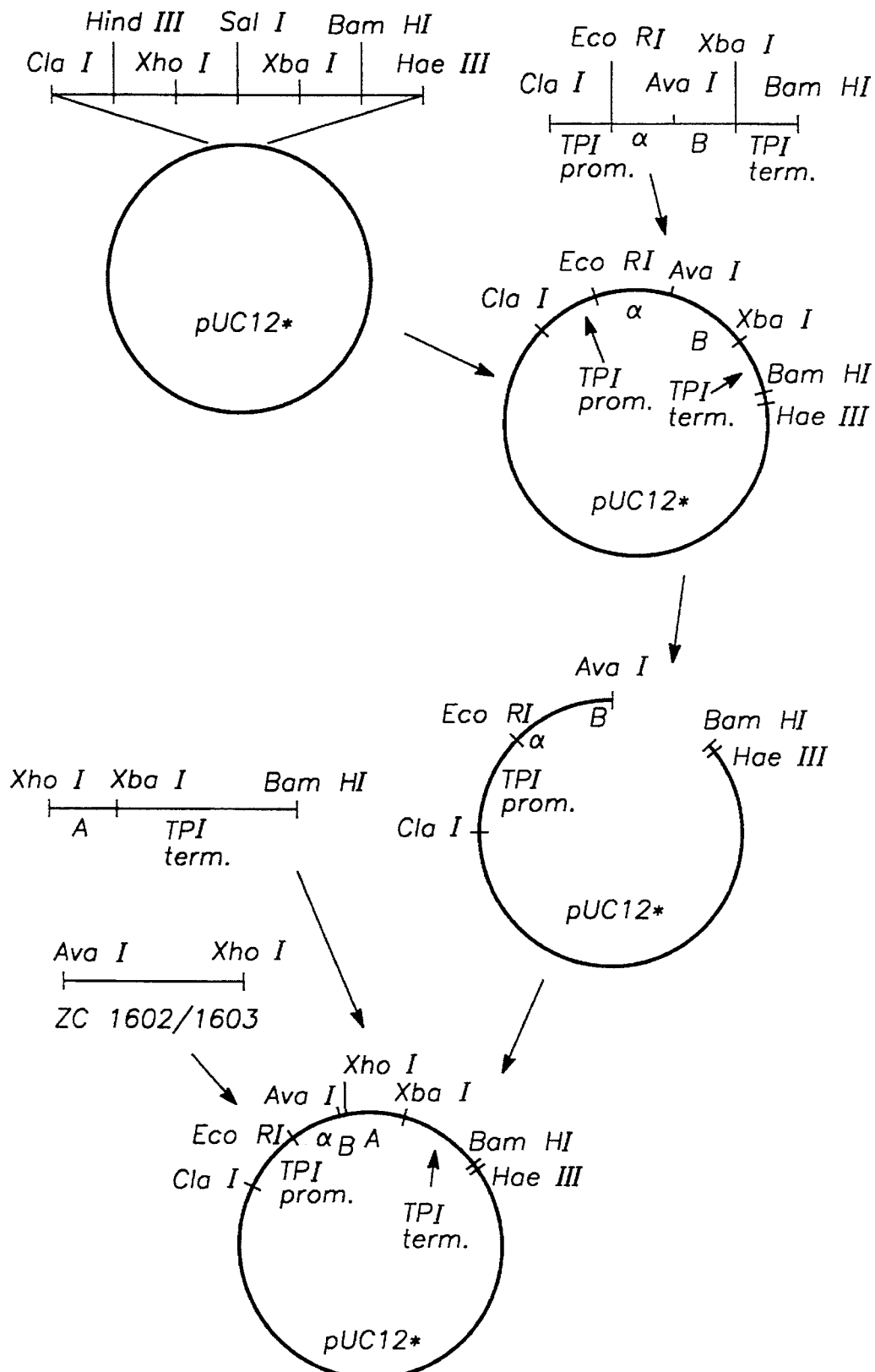
FIG. 4 illustrates the construction of the B/A53 expression unit. Symbols are used as in FIGS. 1 and 2.

A hybrid sequence encoding B-chain amino acids 1–53 and A-chain amino acids 48–104 was constructed (FIG. 4). The sequence of the encoded polypeptide is shown in FIG. 3D. Plasmid pUC12 was linearized by digestion with Hind III and Eco RI. Oligonucleotides ZC1016 and ZC1017 (Table 2) were kinased and annealed to form a polylinker adapter comprising Cla I, Hind III, Xho I, Acc I, Xba I and Bam HI restriction sites. The linear vector was joined with the kinased and annealed ZC1016/ZC1017 adapter by ligation, resulting in the loss of the pUC12 Hind III and Eco RI sites. The resultant vector, pUC12*, was linearized by digestion with Cla I and Bam HI and was joined to a 2.2 kb Cla I-Bam HI fragment containing the expression unit for the codon-optimized B-chain sequence. The resulting plasmid was cut with Ava I and Bam HI and the 4.1 kb fragment was isolated. The A7 expression unit was digested with Xho I and Bam HI and the 842 bp A-chain fragment was isolated. Oligonucleotides ZC1602 and ZC1603 (Table 2) were annealed under standard conditions. The three fragments (4.1 kb vector/B-chain, 842 bp A-chain and ZC1602/1603 duplex) were joined in a three-part ligation (FIG. 4). The presence of the correct construction was confirmed by sequence analysis of an Eco RI-Hind III B/A fragment cloned into M13mp18. A sequence-confirmed clone was digested with Cla I and Bam HI and the 2.2 kb expression unit was cloned into Cla I, Bam HI-cut pMPOT2. This vector was designated pB/A53m.

In a similar manner, a hybrid sequence encoding B-chain amino acids 1–54 joined to A-chain amino acids 49–104 (FIG. 3E) was constructed. This sequence encodes a hybrid polypeptide with a glycosylation site at the A/B junction and was constructed as described for B/A53 except that oligonucleotides ZC1600 and ZC1601 (Table 2) were used. The final pMPOT2-based expression vector is designated pB/A54m.

H. Construction of pA/B59

Figure 5:
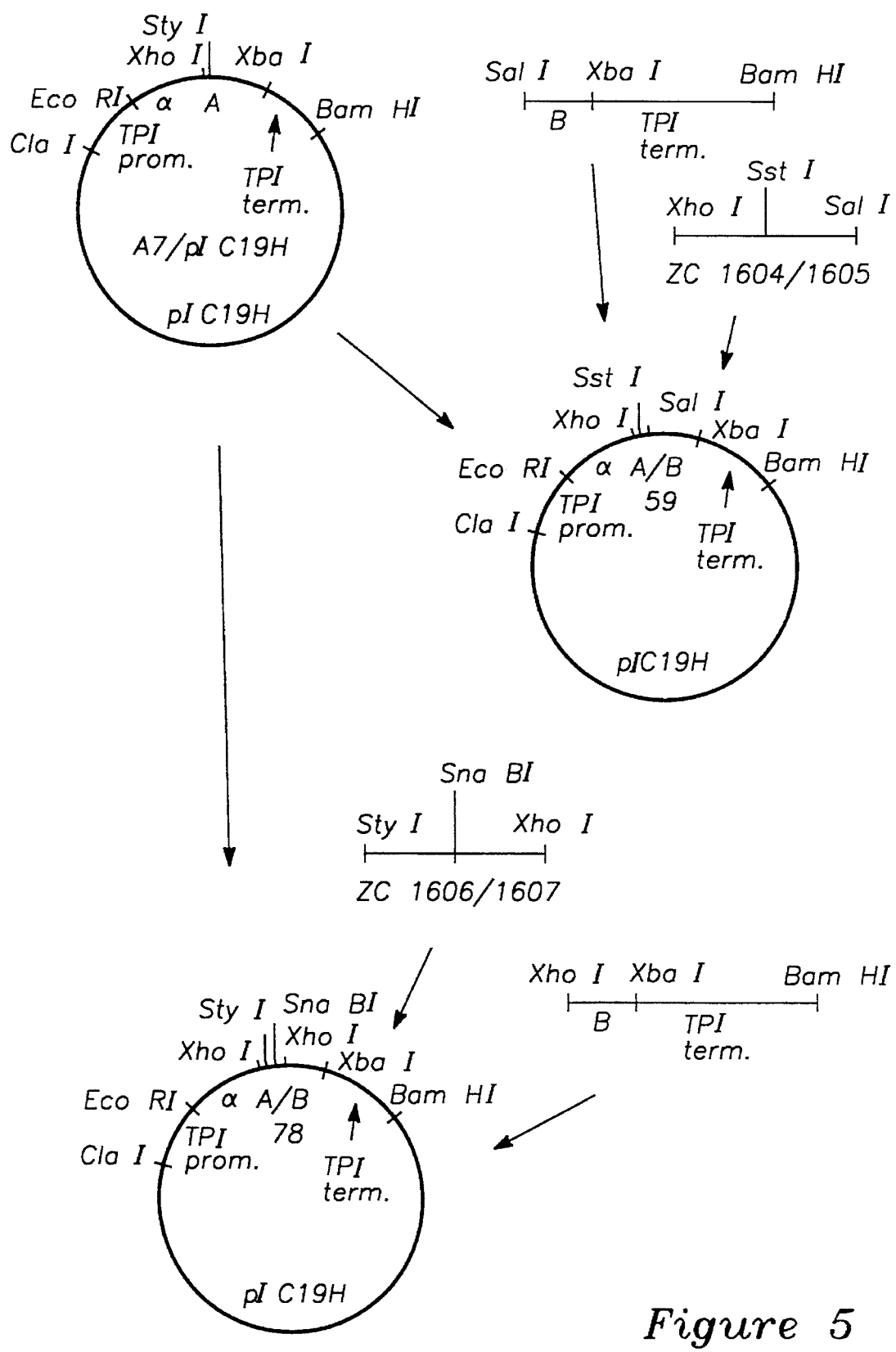
FIG. 5 illustrates the construction of the A/B59 and A/B78 expression units. Symbols are used as in FIGS. 1 and 2.

A sequence encoding A-chain amino acids 1–52 joined to B-chain amino acids 59–109 was constructed, as shown in FIG. 5. The sequence of the encoded polypeptide is shown in FIG. 3F. A Cla I-Bam HI fragment comprising the A7 expression unit was cloned into pIC19H to construct plasmid A7/pIC19H (FIG. 5). This plasmid was digested with Xho I and Bam HI and the 4.0 kb fragment containing the vector and 5' A-chain sequence was isolated. The codon optimized B-chain expression unit was digested with Sal I and Bam HI and the 828 bp fragment was isolated. Oligonucleotides ZC1604 and ZC1605 (Table 2) were annealed under standard conditions. The three fragments (4.0 kb vector/A-chain, B-chain and ZC1604/1605 duplex) were joined in a three-part ligation. The resultant plasmids are screened for the appearance of an Sst I site. Positive clones are confirmed by sequence analysis of an Eco RI-Xba I fragment cloned into M13mp18. Plasmid DNA is prepared from a confirmed positive clone and digested with Cla I and Bam HI to isolate the expression unit, which is then inserted into Cla I, Bam HI-cut pMPOT2 to construct the expression vector pA/B59m.

I. Construction of pA/B78

A sequence encoding A-chain amino acids 1–71 joined to B-chain amino acids 78–109 was constructed, as shown in FIG. 5. The sequence of the encoded polypeptide is shown in FIG. 3G. Plasmid A7/pIC19H was digested with Sty I and Bam HI and the 4.1 kb fragment containing the vector and 5' A-chain sequence was isolated. The codon optimized B-chain expression unit was digested with Xho I and Bam HI and the 736 bp fragment was isolated. Oligonucleotides ZC1606 and ZC1607 (Table 2) were annealed under standard conditions. The three fragments (4.1 kb vector/A-chain, B-chain and ZC1606/1607 duplex) were joined in a three-part ligation. The resultant plasmids were screened for the appearance of an Sna BI site. Positive clones were confirmed by sequence analysis of a ca. 300 bp Asp 718-Xba I fragment cloned into M13mp18. Plasmid DNA was prepared from a confirmed positive clone and digested with Cla I and Bam HI to isolate the expression unit, which was then inserted into Cla I, Bam HI-cut pMPOT2 to construct the expression vector pA/B78m.

S. cerevisiae strain E18 #9 (MATa leu2, 3–112 his4–580 tpi1::LEU2/MATα leu2,3–112 pep4-3 tpi1::LEU2; ATCC 20743) was transformed with pA/B7m. Transformants were grown for two days at 30° C. in fermentation medium. Cells were harvested and the medium was assayed for mitogenic activity. Results indicated that the transformants produced approximately 1400 ng/ml of PDGF activity.

EXAMPLE 3

Expression of A-Chain Variants

A. Endothelial Cell A-Chain

A cDNA clone obtained from an endothelial cell library (Tong et al., *Nature* 328:619–621, 1987) was found to contain a coding sequence for a 110 amino acid A-chain polypeptide. This polypeptide contains the carboxyl terminal sequence Glu-Asp-Thr-Asp-Val-Arg.

The coding sequence for a 110 amino acid A-chain was constructed by mutagenizing the 106 amino acid A-chain coding sequence using the one primer method. Plasmid pA7 was digested with Hind III and Xba I and the 84 bp A-chain fragment was isolated and cloned into M13mp19 which had been linearized by digestion with the same enzymes. Single stranded template DNA was prepared and annealed to oligonucleotide ZC1370 (Table 2). The primer was extended to loop in the codons for the additional four amino acids. Plaques were screened by hybridization to the $^{32}$P-labeled mutagenic oligonucleotide and the inserts of positive clones were verified by sequencing. A confirmed positive clone was selected and digested with Hind III and Xba I to isolate the 102 bp A-chain fragment. This fragment was cloned into Hind III, Xba I-cut plasmid A7CB/pBR (a plasmid identical to pKP33, see Example 1 and FIG. 6). The resultant expression unit, termed A8, was isolated from the pBR322 vector as a Cla I-Bam HI fragment, and was inserted into Cla I, Bam HI-cut pMPOT2. The resultant vector was designated pA8m. The amino acid sequence of the encoded protein is shown in FIG. 3H.

Plasmid pA8m was transformed into *S. cerevisiae* strain E18#9 and transformants were cultured in fermentation medium at 30° C. for 24–48 hours. Cells were harvested and the medium was assayed for mitogenic activity. The A8 protein was found to be of comparable mitogenic activity to the A7 protein.

B. Glioma Cell A-Chain

Analysis of a cDNA cloned from a glioma cell line (Betsholtz et al., *Nature* 320:695–699, 1986) identified a sequence encoding a 125 amino acid A-chain polypeptide. This polypeptide has the C-terminal sequence Glu(104)-Glu-Asp-Thr-Gly-Arg-Pro-Arg-Glu-Ser-Gly-Lys-Lys-Arg-Lys-Arg-Lys-Arg-Leu-Lys-Pro-Thr (125).

To prepare a 125 amino acid A-chain coding sequence, a sequence-confirmed A8 Hind III-Xba I sequence in M13mp19 was used to prepare a template for mutagenesis. The 3' end of the A-chain sequence was modified and extended by site-specific mutagenesis using the mutagenic primer ZC1462 (Table 2). Plaques were screened by hybridization to $^{32}$P-labeled ZC1462, and positive clones were confirmed by sequence analysis. A positive clone was selected and digested with Hind III and Xba I to isolate the 147 bp A-chain fragment. This fragment was cloned into Hind III, Xba I-cut A7CB/pBR. The presence of the desired construction was confirmed by restriction analysis using Hind III and Xba I. The resultant A9 expression unit was isolated as a Cla I-Bam HI fragment and inserted into Cla I, Bam HI-cut pMPOT2 to construct the expression vector pA9m. The sequence of the 125 amino acid A-chain is shown in FIG. 3I.

Vector pA9m was transformed into *S. cerevisiae* strain E18#9. Transformants were grown in fermentation medium at 30° C. for 24–48 hours. Cells were removed and the culture medium was assayed for PDGF receptor-binding activity by the radioreceptor assay. The A9 protein was found to be active.

EXAMPLE 4

PDGF Heterodimer Expression Vector

Figure 6:
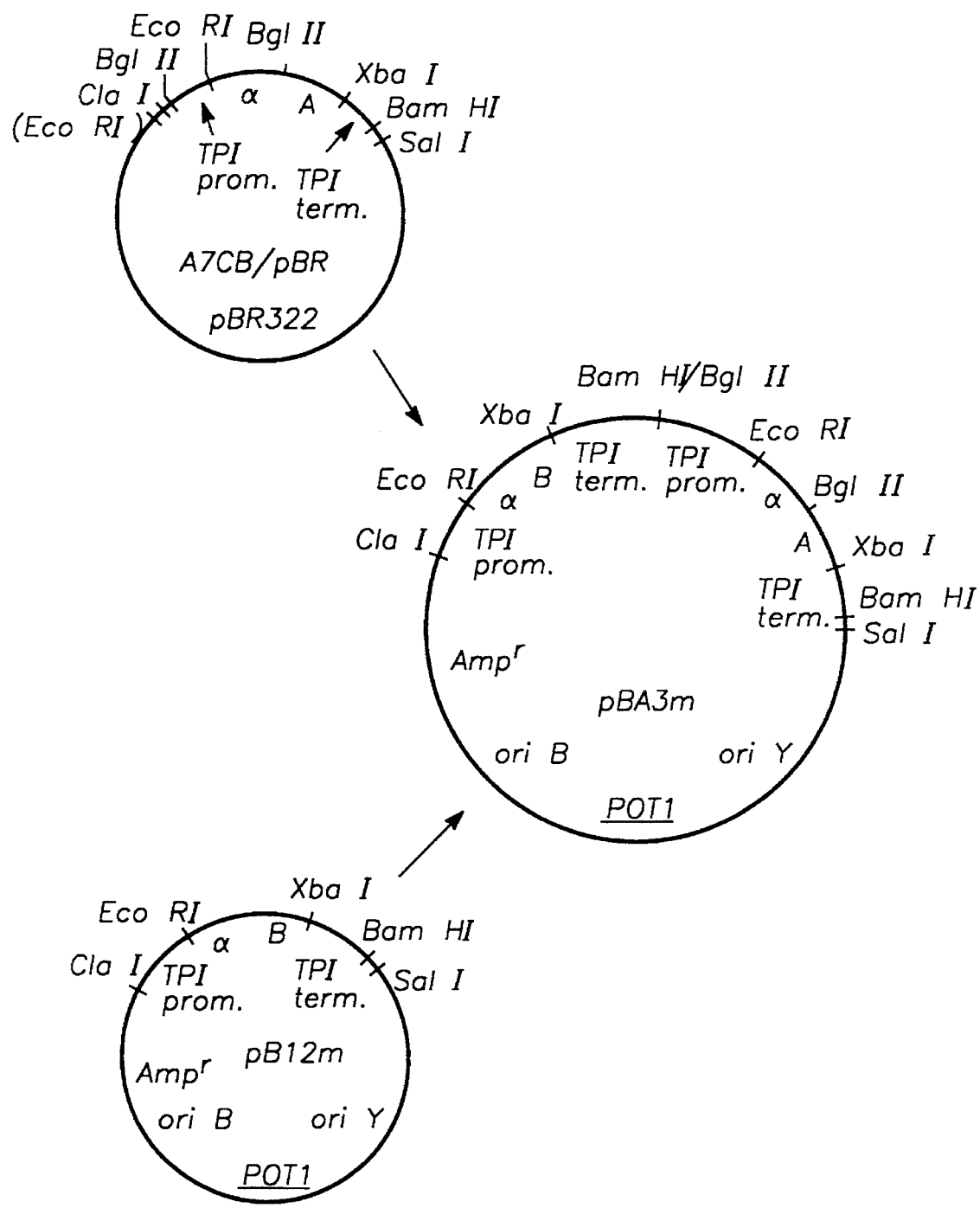
FIG. 6 illustrates the construction of an expression vector for PDGF heterodimer. Symbols are used as in FIGS. 1 and 2.

A vector comprising A-chain and B-chain expression units in tandem was prepared, as shown in FIG. 6. Plasmid A7CB/pBR was partially digested with Bgl II and completely digested with Sal I and the ca. 2.5 kb fragment comprising the A-chain expression unit was isolated. Plasmid pB12m (Murray et al., U.S. Ser. No. 896,485), a pMPOT2 derivative containing an expression unit for the human PDGF B-chain (FIG. 6), was linearized by digestion with Bam HI and Sal I and the A7 fragment was inserted. The resultant plasmids were screened by restriction mapping and a clone having the desired construction was selected and designated pBA3m.

The heterodimer expression units are isolated from pBA3m as a Cla I-Bam HI fragment and cloned into Cla I, Bam HI-digested pRPOT. (The vector pRPOT was derived from pCPOT (ATCC 39685) by first replacing the 750 bp Sph I-Bam HI fragment of pCPOT with a 186 bp Sph I-Bam HI fragment of pBR322. The resultant plasmid, pDPOT, was digested with Sph I and Bam HI to isolate the 10.8 kb fragment. Oligonucleotides ZC1551 and ZC1552 (Table 2) were kinased and annealed to form an adaptor with a Bam HI adhesive end and an Sph I adhesive end flanking Sma I, Sst I and Xho I restriction sites. The 10.8 kb pDPOT fragment was then joined to the adaptor to construct pRPOT). The resultant expression vector is designated pBA3R.

Expression vector pBA3R is used to transform *S. cerevisiae* strain XB13–5B. Cultures are grown in fermentation medium at 30° C. with agitation. Cultures are harvested, cells are removed by centrifugation and the supernatants are recovered. The AB heterodimer is isolated by immobilized metal affinity chromatography essentially as described by Sulkowski (ibid.) and Porath et al. (ibid.)

EXAMPLE 5

Biological Activity of PDGF Analogs

The biological activities of several recombinant PDGF analogs were compared to those of native platelet PDGF. The proteins were assayed for mitogenic activity, receptor binding activity and promotion of wound healing in an animal model.

Figure 7A:
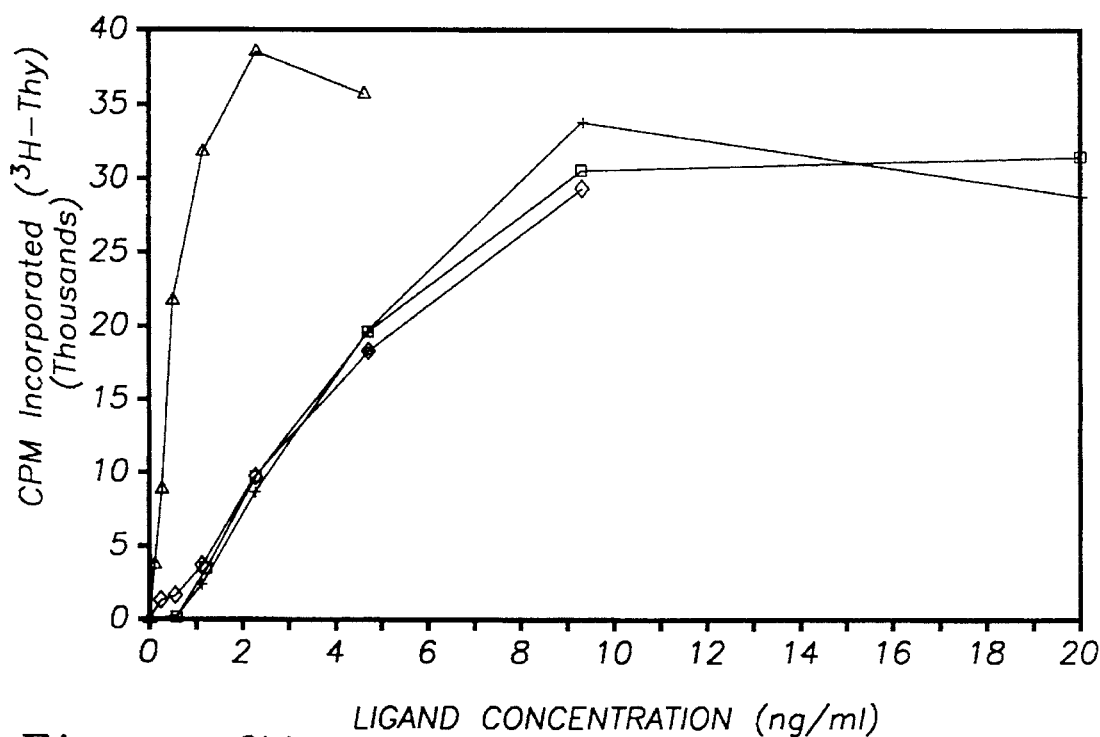
FIGS. 7A and 7B illustrate the results of mitogenesis assays on several PDGF analogs. Symbols used are □, 110 amino acid AA; +, 106 amino acid AA; ◊, recombinant BB; ∆, platelet AB.
Figure 7B:
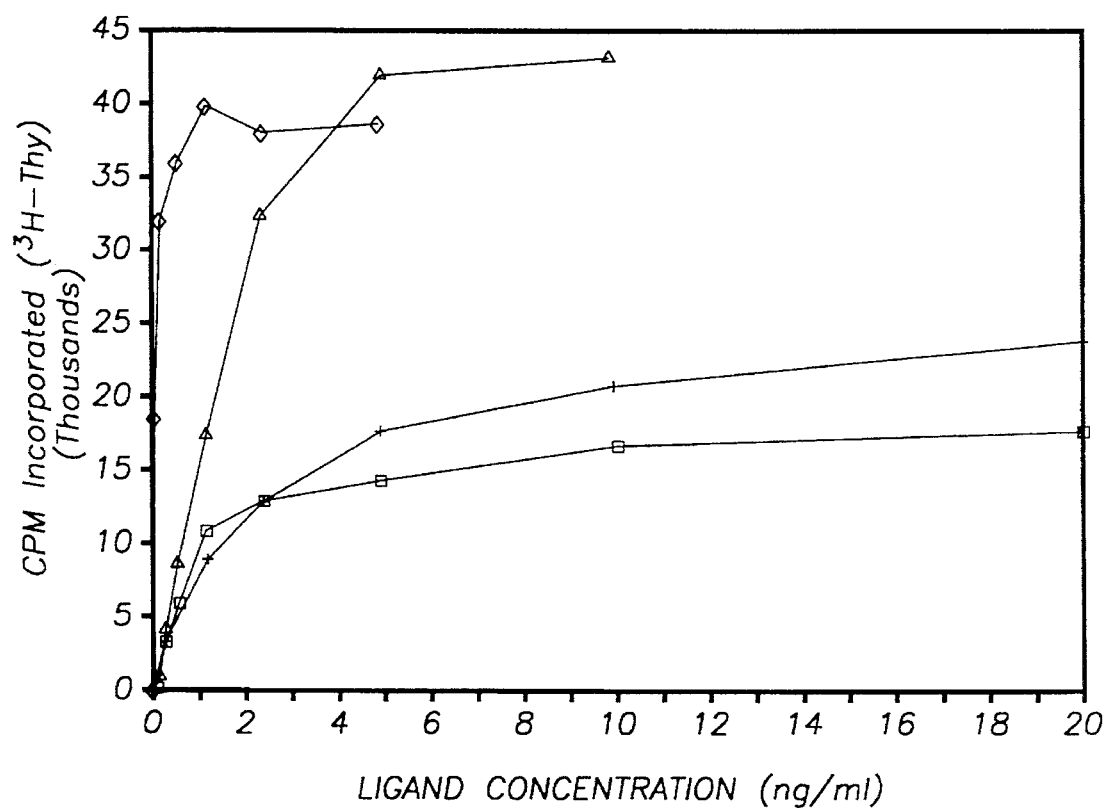

Mitogenesis assays measured effects on two different cell types, Swiss 3T3 cells and human dermal fibroblasts (Sk-5), comparing platelet-derived AB, recombinant BB (from plasmid pB170m), recombinant 110 amino acid AA homodimer and recombinant 106 amino acid (pA7-derived) AA homodimer. The results show that on 3T3 cells (FIG. 7) the three recombinant forms of PDGF are nearly identical for stimulating 3H-thymidine incorporation. The AB material is a more potent mitogen, stimulating the cells at lower doses, but has approximately equal activity with AA and BB for maximal stimulation. In contrast, the two AA proteins are approximately equal for mitogenic activity on the Sk-5 cells (FIG. 7), but have only about one-half the maximal stimulatory response as that elicited by either AB or BB forms. The differences in the results between the two cell lines may reflect differences in PDGF receptor expression.

Figure 8:
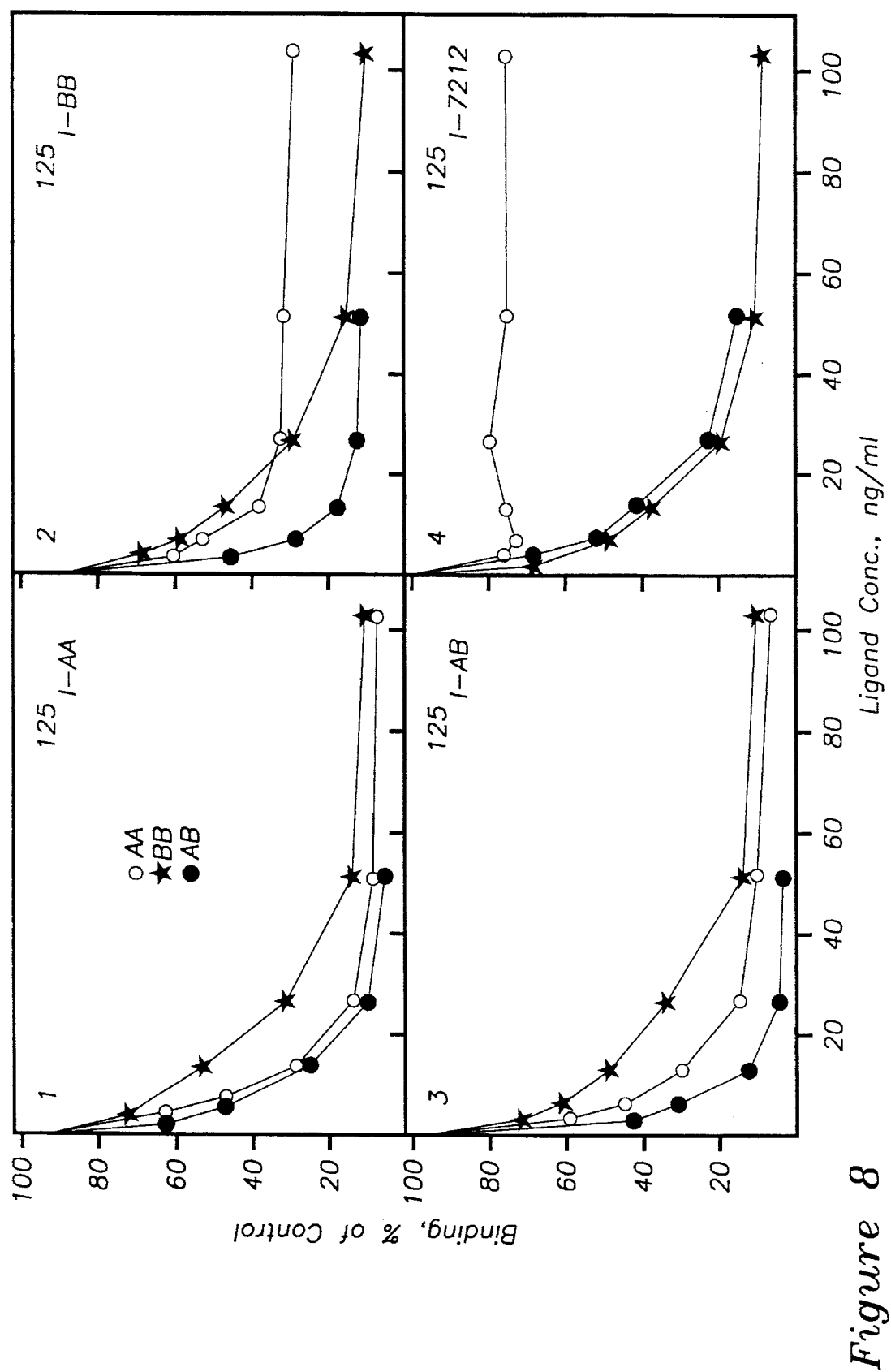
FIG. 8 illustrates the results of down regulation assays on several PDGF analogs. Receptor expression was measured using $^{125}$I-labeled AA, BB, AB or anti-receptor antibody 7212.

Receptor binding was measured in a down regulation assay (DRA). Briefly, this assay monitors receptor binding by the test ligand at 37° C. and the subsequent stimulation of receptor internalization from the cell surface. The decrease in receptor expression is then monitored by the subsequent addition of $^{125}$I-labeled ligand or antibody at 4° C. The results (FIG. 8) show that on MG-63 cells all three isoforms of PDGF have equal maximal effect in reducing subsequent binding of $^{125}$I-labeled AA and AB. AB and BB equally stimulate maximal loss of $^{125}$I-BB binding while AA stimulates only a 50–75% decrease in $^{125}$I-BB binding.

Figure 9:
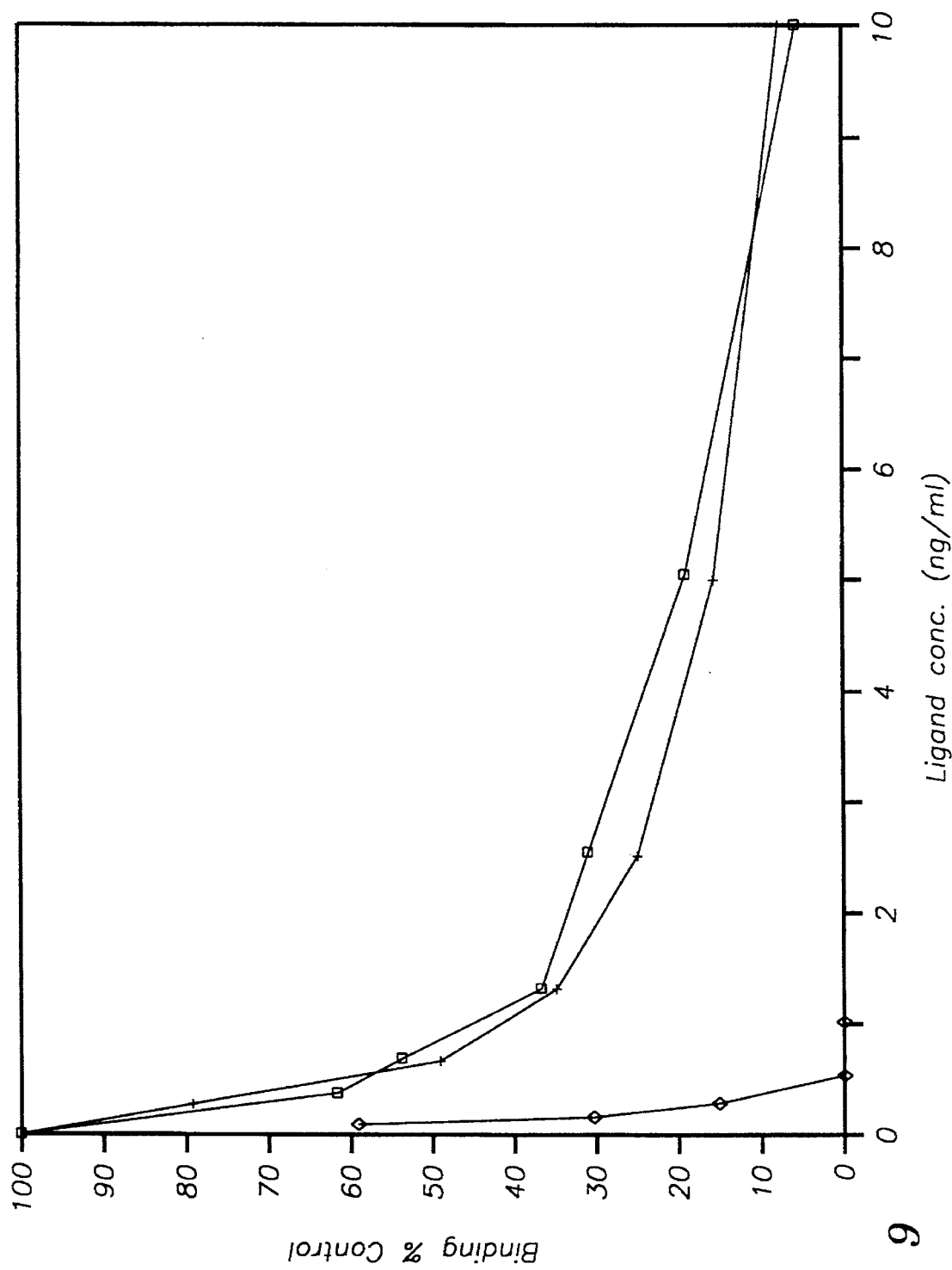
FIG. 9 illustrates the results of radioreceptor assays on PDGF A-chain homodimers. Symbols used are □, 106 amino acid AA; +, 110 amino acid AA; ◊, platelet AB.

The two AA homodimers were also examined for their ability to compete for receptor binding in a radio receptor assay. The results (FIG. 9) show that both A-chain constructions compete equally with $^{125}$I-labeled AB on a molar basis for receptor binding. In contrast AB competes for receptor binding at much lower doses.

The effectiveness of PDGF B-chain homodimer (prepared essentially as described in Example 1 using pB170m) and basic fibroblast growth factor (bFGF) in stimulating wound repair was studied in normal and diabetic mice. This animal wound model used the congenitally diabetic C57BL/KsJ-dbm (db/db) mouse (Jackson Laboratories, Bar Harbor, Me.). These animals are hyperglycemic and insulin-resistant. Heterozygote litter mates (not expressing the diabetic phenotype) were used as controls. Typically, untreated, full-thickness skin wounds on the nondiabetic control mice completely close by 14 days after surgery. The area decreases approximately 85% by contraction and the remaining 15% closes by formation of granulation tissue and epithelial migration. In contrast, untreated wounds on the diabetic mice do not decrease significantly in size in 14 days, nor do they develop much granulation tissue in that time. The wounds on the diabetic mice eventually heal, but the process takes 8–12 weeks. The cause of the healing impairment in these animals is not known.

1.5 cm×1.5 cm full-thickness skin wounds were made on the backs of anesthetized animals and covered with Opsite semi-permeable dressings (Smith and Nephew Medical, Massilion, Ohio). Immediately after wounding and daily for four days thereafter, 0.1 ml of the treatment mixture was injected through the dressing onto the wound bed. The growth factors were mixed with 0.25% mouse serum albumin (MSA) in phosphate-buffered saline for administration. The edges of the wounds were traced on days 0, 1, 2, 3, 4, 7, 10, 15 and 21 after surgery for calculation of open wound area. Ten or 21 days after injury the animals were sacrificed and the wounds were taken for histological and biochemical analysis. Each wound was scored without knowledge of its treatment group by three investigators. Scores were assigned on the basis of the presence/absence, thickness, cellularity and maturity of granulation tissue and the degree of epithelial migration from the wound edge.

Results of the study indicated that treatment with PDGF-BB homodimer enhanced wound healing in the diabetic animals. Injection of 0.25% MSA onto the wound bed did not affect the rate of healing or the development of granulation tissue in the diabetic mice. In the margin of a wound treated with 0.25% MSA 10 days after wounding there was a thin band of loosely organized cells and connective tissue under the migrating epithelium but at the center of the wound bed there were only patchy accumulations of cells. In contrast, administration of 5 µg of recombinant PDGF-BB for 5 days stimulated the formation of granulation tissue in the diabetic mice by 10 days after injury. The band of granulation tissue beneath the epithelium was much thicker and more vascular than in the corresponding control (MSA) mice. There was no difference in the wound size at 10 days between the MSA and PDGF-BB treated wounds.

Treatment of the wounds in diabetic mice with 0.4 µg recombinant basic FGF also stimulated a granulation tissue response by 10 days after injury. While there was no effect on the open area of the wounds at 10 days, by 21 days after injury, wounds treated with a combination of 5 µg PDGF BB and 0.4 µg bFGF were 13% ± 9% of their original area while the vehicle treated wounds were 38%±8% of their original area.

A second series of experiments tested the efficacy of recombinant BB and recombinant bFGF in a polyethylene glycol (PEG) carrier in the same animal model. Full-thickness skin wounds (1.5×1.5 cm) were made in the paravertebral region of the anesthetized animals and covered with Opsite. Immediately after wounding and daily for four days thereafter, 0.1 ml of the treatment mixture was injected through the dressing and onto the wound bed. Test animals, both diabetic and normal, received recombinant BB (1 µg or 10 µg) or bFGF (0.4 µg) in 5% PEG in phosphate buffered saline. Controls received PEG alone. The edges of the wounds were traced onto a glass slide and the wound areas were determined using computerized planimetry. Ten or 21 days after wounding the animals were sacrificed and the wounds were taken for histologic and biochemical analyses. Histologic scores were assigned on the basis of the presence or absence, thickness, cellularity and maturity of granulation tissue and the degree of epithelial migration from the wound edge.

The 10-day results indicated that both recombinant growth factors stimulate the formation of granulation tissue and accelerate wound closure in the diabetic mice at the doses tested. Either growth factor consistently produced wounds with higher histologic scores. The treated diabetic animals had markedly thicker, more cellular and more vascular granulation at day 10 than the control diabetics.

Results after 21 days also indicate that BB and bFGF promote wound healing in the diabetic animals. Data are presented in Table 5. The histological score indicates the degree of wound healing on a scale of 1 (no healing) to 12 (full re-epithelialization with mature granulation tissue).

TABLE 5

| Treatment | n | Histol. Score (Median, range) | % Wound Closure (Mean ± SD) |
|---|---|---|---|
| 5% PEG | 5 | 3(2−, 4−) | 63.7 ± 19.4% |
| 1 µgBB | 5 | 3(3, 4+) | 77.6 ± 13.0 |
| 0.4 µg bFGF | 5 | 4(3+, 4+) | 93.3 ± 3.7 |
| 1 µgBB + 0.4 µgbFGF | 4 | 3(3−, 4+) | 80.4 ± 16.0 |

We claim:

1. An unglycosylated protein homodimer having two polypeptide chains, each of said chains being a mosaic of amino acid sequences substantially identical to portions of the A- or B-chains of PDGF, said protein being chemotactic or mitogenic for fibroblasts.

2. A therapeutic composition comprising an unglycosylated protein homodimer having two polypeptide chains, each of said chains being a mosaic of amino acid sequences substantially identical to portions of the A- or B- chains of PDGF, said protein being chemotactic or mitogenic for fibroblasts, and a physiologically acceptable carrier or diluent.

3. A method for enhancing the wound-healing process in warm-blooded animals, comprising administering to the animal a therapeutically effective amount of a composition comprising an unglycosylated protein homodimer having two polypeptide chains, each of said chains being a mosaic of amino acid sequences substantially identical to portions of the A- or B-chains of PDGF, said protein being chemotactic or mitogenic for fibroblasts, and a physiologically acceptable carrier.

4. The method of claim 3 wherein said carrier is selected from the group consisting of albumin, sterile water, polyethylene glycol and saline.

5. The method of claim 3 wherein said composition includes an adjuvant.

6. The method of claim 3 wherein said composition is administered topically.

7. The method of claim 3 wherein said composition is administered in a dose of from about 0.5 to about 10 µg per $cm^2$ of wound area.

8. The method of claim 3 wherein said composition includes an effective amount of basic fibroblast growth factor.

9. The method of claim 8 wherein the protein homodimer and the fibroblast growth factor are present in a ratio of from approximately 1 to 0.4, to 10 to 0.4, respectively.

10. The method of claim 3 wherein said warm-blooded animal is a diabetic animal.

* * * * *